(12) United States Patent
Levine et al.

(10) Patent No.: US 7,819,836 B2
(45) Date of Patent: Oct. 26, 2010

(54) RESISTIVE ANTI-OBESITY DEVICES

(75) Inventors: Andy H. Levine, Newton, MA (US);
Ronald B. Lamport, Pelham, NH (US);
David A. Melanson, Hudson, NH (US);
Stuart A. Randle, Concord, MA (US);
Ezra S. Fishman, Cambridge, MA (US)

(73) Assignee: GI Dynamics, Inc., Lexington, MA (US)

( * ) Notice: Subject to any disclaimer, the term of this patent is extended or adjusted under 35 U.S.C. 154(b) by 596 days.

(21) Appl. No.: 11/827,674

(22) Filed: Jul. 12, 2007

(65) Prior Publication Data

US 2008/0071383 A1    Mar. 20, 2008

Related U.S. Application Data

(63) Continuation of application No. 11/821,551, filed on Jun. 22, 2007, now abandoned.

(60) Provisional application No. 60/816,143, filed on Jun. 23, 2006.

(51) Int. Cl.
*A61M 5/00* (2006.01)
*A61F 2/04* (2006.01)
*A61B 18/18* (2006.01)

(52) U.S. Cl. ............... 604/9; 604/8; 606/37; 623/23.68

(58) Field of Classification Search ............... 604/8, 604/9; 606/37; 623/23.68
See application file for complete search history.

(56) References Cited

U.S. PATENT DOCUMENTS

| | | | |
|---|---|---|---|
| 4,246,893 A | 1/1981 | Berson | |
| 4,265,694 A | 5/1981 | Boretos et al. | |
| 4,271,827 A | 6/1981 | Angelchik | |
| 4,315,509 A | 2/1982 | Smit | |
| 4,341,218 A | 7/1982 | U | |
| 4,617,932 A | 10/1986 | Kornberg | |
| 4,768,507 A | 9/1988 | Fischell et al. | |

(Continued)

FOREIGN PATENT DOCUMENTS

EP    0 506 918 B1    1/1996

(Continued)

OTHER PUBLICATIONS

Choostent™, Covered Esophageal Stent, Instructions, Retrieved from the Internet (http://mitech.co.kr/uploads/images/282/use guide esophachoo_english.pdf) on Jul. 26, 2005.

(Continued)

*Primary Examiner*—Leslie R Deak
(74) *Attorney, Agent, or Firm*—Hamilton, Brook, Smith & Reynolds, P.C.

(57) ABSTRACT

A patient is provided with an increased sense of satiety by increasing resistance to the outflow of food from the stomach and through the intestines. Stomach emptying may be slowed with devices implantable within the gastrointestinal tract below the stomach. Implants are preferably removable and can include artificial strictures or apertures that may be adjustable or elastic to vary the rate of stomach emptying. Slowing gastric emptying may induce satiety for a longer period and may therefore reduce food consumption. Many of the embodiments include intestinal sleeves or sleeves, but they need not. The resistor concept may be applied to a simple anchor and resistor without a long sleeve.

35 Claims, 17 Drawing Sheets

U.S. PATENT DOCUMENTS

| | | | |
|---|---|---|---|
| 4,846,836 A | 7/1989 | Reich | |
| 4,905,693 A | 3/1990 | Ravo | |
| 4,913,141 A | 4/1990 | Hillstead | |
| 5,037,387 A | 8/1991 | Quinn et al. | |
| 5,059,166 A | 10/1991 | Fischell et al. | |
| 5,104,399 A | 4/1992 | Lazarus | |
| 5,123,917 A | 6/1992 | Lee | |
| 5,135,516 A | 8/1992 | Sahatjian et al. | |
| 5,152,782 A | 10/1992 | Kowligi et al. | |
| 5,176,617 A | 1/1993 | Fischell et al. | |
| 5,190,561 A | 3/1993 | Graber | |
| 5,226,429 A | 7/1993 | Kuzmak | |
| 5,254,133 A | 10/1993 | Seid | |
| 5,290,294 A | 3/1994 | Cox et al. | |
| 5,306,300 A | 4/1994 | Berry | |
| 5,314,473 A | 5/1994 | Godin | |
| 5,322,501 A | 6/1994 | Mahmud-Durrani | |
| 5,330,500 A | 7/1994 | Song | |
| 5,389,090 A | 2/1995 | Fischell et al. | |
| 5,405,378 A | 4/1995 | Strecker | |
| 5,417,697 A | 5/1995 | Wilk et al. | |
| 5,423,851 A | 6/1995 | Samuels | |
| 5,480,423 A | 1/1996 | Ravenscroft et al. | |
| 5,492,530 A | 2/1996 | Fischell et al. | |
| 5,605,530 A | 2/1997 | Fischell et al. | |
| 5,607,442 A | 3/1997 | Fischell et al. | |
| 5,634,928 A | 6/1997 | Fischell et al. | |
| 5,639,274 A | 6/1997 | Fischell et al. | |
| 5,643,312 A | 7/1997 | Fischell et al. | |
| 5,669,932 A | 9/1997 | Fischell et al. | |
| 5,695,516 A | 12/1997 | Fischell et al. | |
| 5,697,971 A | 12/1997 | Fischell et al. | |
| 5,720,776 A | 2/1998 | Chuter et al. | |
| 5,722,984 A | 3/1998 | Fischell et al. | |
| 5,730,698 A | 3/1998 | Fischell et al. | |
| 5,733,325 A | 3/1998 | Robinson et al. | |
| 5,735,859 A | 4/1998 | Fischell et al. | |
| 5,735,892 A | 4/1998 | Myers et al. | |
| 5,743,874 A | 4/1998 | Fischell et al. | |
| 5,749,825 A | 5/1998 | Fischell et al. | |
| 5,759,174 A | 6/1998 | Fischell et al. | |
| 5,792,144 A | 8/1998 | Fischell et al. | |
| 5,792,172 A | 8/1998 | Fischell et al. | |
| 5,820,584 A * | 10/1998 | Crabb | 604/500 |
| 5,830,229 A | 11/1998 | Konya et al. | |
| 5,840,009 A | 11/1998 | Fischell et al. | |
| 5,843,164 A | 12/1998 | Frantzen et al. | |
| 5,855,601 A | 1/1999 | Bessler et al. | |
| 5,876,445 A | 3/1999 | Andersen et al. | |
| 5,879,282 A | 3/1999 | Fischell et al. | |
| 5,879,370 A | 3/1999 | Fischell et al. | |
| 5,910,145 A | 6/1999 | Fischell et al. | |
| 5,913,895 A | 6/1999 | Burpee et al. | |
| 5,919,233 A | 7/1999 | Knopf et al. | |
| 5,925,063 A | 7/1999 | Khosravi | |
| 5,962,620 A | 10/1999 | Reich et al. | |
| 5,976,153 A | 11/1999 | Fischell et al. | |
| 6,013,019 A | 1/2000 | Fischell et al. | |
| 6,027,508 A | 2/2000 | Ren et al. | |
| 6,027,526 A | 2/2000 | Limon et al. | |
| 6,086,604 A | 7/2000 | Fischell et al. | |
| 6,102,887 A | 8/2000 | Altman | |
| 6,120,533 A | 9/2000 | Fischell | |
| 6,120,534 A | 9/2000 | Ruiz | |
| 6,146,323 A | 11/2000 | Fischell | |
| 6,152,956 A | 11/2000 | Pierce | |
| 6,179,868 B1 | 1/2001 | Burpee et al. | |
| 6,187,016 B1 | 2/2001 | Hedges et al. | |
| 6,190,403 B1 | 2/2001 | Fischell et al. | |
| 6,221,043 B1 | 4/2001 | Fischell et al. | |
| 6,221,102 B1 | 4/2001 | Baker et al. | |
| 6,241,757 B1 | 6/2001 | An et al. | |
| 6,251,064 B1 | 6/2001 | Silverman et al. | |
| 6,270,521 B1 | 8/2001 | Fischell et al. | |
| 6,302,891 B1 | 10/2001 | Nadal | |
| 6,302,917 B1 | 10/2001 | Dua et al. | |
| 6,315,708 B1 | 11/2001 | Salmon et al. | |
| 6,355,056 B1 | 3/2002 | Pinheiro | |
| 6,356,782 B1 | 3/2002 | Sirimanne et al. | |
| 6,375,660 B1 | 4/2002 | Fischell et al. | |
| 6,383,214 B1 | 5/2002 | Banas et al. | |
| 6,401,718 B1 | 6/2002 | Johnson et al. | |
| 6,402,779 B1 | 6/2002 | Colone et al. | |
| 6,406,792 B1 | 6/2002 | Briquet et al. | |
| 6,458,074 B1 | 10/2002 | Matsui et al. | |
| 6,485,515 B2 | 11/2002 | Strecker | |
| 6,520,985 B1 | 2/2003 | Burpee et al. | |
| 6,540,775 B1 | 4/2003 | Fischell et al. | |
| 6,540,789 B1 | 4/2003 | Silverman et al. | |
| 6,544,291 B2 | 4/2003 | Taylor | |
| 6,547,817 B1 | 4/2003 | Fischell et al. | |
| 6,558,429 B2 | 5/2003 | Taylor | |
| 6,623,518 B2 | 9/2003 | Thompson et al. | |
| 6,635,069 B1 | 10/2003 | Teoh et al. | |
| 6,635,079 B2 | 10/2003 | Unsworth et al. | |
| 6,645,239 B1 | 11/2003 | Park et al. | |
| 6,652,555 B1 | 11/2003 | VanTassel et al. | |
| 6,669,722 B2 | 12/2003 | Chen et al. | |
| 6,675,809 B2 | 1/2004 | Stack et al. | |
| 6,676,692 B2 | 1/2004 | Rabkin et al. | |
| 6,699,278 B2 | 3/2004 | Fischell et al. | |
| 6,706,061 B1 | 3/2004 | Fischell et al. | |
| 6,716,240 B2 | 4/2004 | Fischell et al. | |
| 6,736,840 B2 | 5/2004 | Fischell et al. | |
| 6,740,121 B2 | 5/2004 | Geitz | |
| 6,764,518 B2 | 7/2004 | Godin | |
| 6,773,440 B2 | 8/2004 | Gannoe et al. | |
| 6,776,791 B1 | 8/2004 | Stallings et al. | |
| 6,802,868 B2 | 10/2004 | Silverman et al. | |
| 6,821,291 B2 | 11/2004 | Bolea et al. | |
| 6,845,776 B2 | 1/2005 | Stack et al. | |
| 6,860,901 B1 | 3/2005 | Baker et al. | |
| 6,936,065 B2 | 8/2005 | Khan et al. | |
| 6,960,233 B1 | 11/2005 | Berg et al. | |
| 7,011,673 B2 | 3/2006 | Fischell et al. | |
| 7,025,791 B2 | 4/2006 | Levine et al. | |
| 7,037,327 B2 | 5/2006 | Salmon et al. | |
| 7,037,344 B2 | 5/2006 | Kagan et al. | |
| 7,081,132 B2 | 7/2006 | Cook et al. | |
| 7,087,088 B2 | 8/2006 | Berg et al. | |
| 7,121,283 B2 | 10/2006 | Stack et al. | |
| 7,122,058 B2 | 10/2006 | Levine et al. | |
| 7,146,984 B2 | 12/2006 | Stack et al. | |
| 7,152,607 B2 | 12/2006 | Stack et al. | |
| 7,160,312 B2 | 1/2007 | Saadat | |
| 7,175,660 B2 | 2/2007 | Cartledge et al. | |
| 7,211,114 B2 | 5/2007 | Bessler et | |
| 7,220,237 B2 | 5/2007 | Gannoe et al. | |
| 7,220,284 B2 | 5/2007 | Kagan et al. | |
| 7,267,694 B2 | 9/2007 | Levine et al. | |
| 7,314,489 B2 | 1/2008 | McKenna et al. | |
| 7,329,285 B2 | 2/2008 | Levine et al. | |
| 7,338,520 B2 | 3/2008 | Bailey et al. | |
| 7,347,875 B2 | 3/2008 | Levine et al. | |
| 7,354,454 B2 | 4/2008 | Stack et al. | |
| 7,476,256 B2 | 1/2009 | Meade et al. | |
| 2001/0020190 A1 | 9/2001 | Taylor | |
| 2002/0022853 A1 | 2/2002 | Swanson et al. | |
| 2002/0032487 A1 | 3/2002 | Dua et al. | |
| 2002/0065545 A1 | 5/2002 | Leonhardt et al. | |
| 2002/0091439 A1 | 7/2002 | Baker et al. | |
| 2002/0147489 A1 | 10/2002 | Hong et al. | |
| 2002/0183786 A1 | 12/2002 | Girton | |
| 2002/0188344 A1 | 12/2002 | Bolea et al. | |

| | | |
|---|---|---|
| 2002/0188354 A1 | 12/2002 | Peghini |
| 2003/0040804 A1 | 2/2003 | Stack et al. |
| 2003/0040808 A1 | 2/2003 | Stack et al. |
| 2003/0109931 A1 | 6/2003 | Geitz |
| 2003/0153927 A1 | 8/2003 | DiPoto et al. |
| 2003/0191476 A1 | 10/2003 | Smit |
| 2003/0199991 A1 | 10/2003 | Stack et al. |
| 2003/0216749 A1 | 11/2003 | Ishikawa et al. |
| 2004/0019388 A1 | 1/2004 | Starkebaum |
| 2004/0037865 A1 | 2/2004 | Miller |
| 2004/0039452 A1 | 2/2004 | Bessler |
| 2004/0082963 A1 | 4/2004 | Gannoe et al. |
| 2004/0092892 A1 | 5/2004 | Kagan et al. |
| 2004/0092974 A1 | 5/2004 | Gannoe et al. |
| 2004/0093065 A1 | 5/2004 | Yachia et al. |
| 2004/0107004 A1 | 6/2004 | Levine et al. |
| 2004/0117004 A1 | 6/2004 | Osborne et al. |
| 2004/0117031 A1 | 6/2004 | Stack et al. |
| 2004/0122470 A1 | 6/2004 | Deem et al. |
| 2004/0122526 A1 | 6/2004 | Imran |
| 2004/0138761 A1 | 7/2004 | Stack et al. |
| 2004/0151740 A1 | 8/2004 | Aoki et al. |
| 2004/0158229 A1 | 8/2004 | Quinn |
| 2004/0172142 A1 | 9/2004 | Stack et al. |
| 2004/0181242 A1 | 9/2004 | Stack et al. |
| 2004/0193093 A1 | 9/2004 | Desmond, III |
| 2004/0193261 A1 | 9/2004 | Berreklouw |
| 2004/0210243 A1 | 10/2004 | Gannoe et al. |
| 2004/0220682 A1 | 11/2004 | Levine et al. |
| 2004/0236401 A1 | 11/2004 | Shin et al. |
| 2004/0249362 A1 | 12/2004 | Levine et al. |
| 2005/0004681 A1 | 1/2005 | Stack et al. |
| 2005/0033331 A1 | 2/2005 | Burnett et al. |
| 2005/0043601 A1 | 2/2005 | Kilcoyne et al. |
| 2005/0043817 A1 | 2/2005 | McKenna et al. |
| 2005/0049718 A1 | 3/2005 | Dann et al. |
| 2005/0055039 A1 | 3/2005 | Burnett et al. |
| 2005/0075622 A1 | 4/2005 | Levine et al. |
| 2005/0080395 A1 | 4/2005 | Levine et al. |
| 2005/0080431 A1 | 4/2005 | Levine et al. |
| 2005/0080491 A1 | 4/2005 | Levine et al. |
| 2005/0085787 A1 | 4/2005 | Laufer |
| 2005/0085923 A1 | 4/2005 | Levine et al. |
| 2005/0090873 A1 | 4/2005 | Imran |
| 2005/0096750 A1 | 5/2005 | Kagan et al. |
| 2005/0111072 A1 | 5/2005 | Miyagaki et al. |
| 2005/0125020 A1 | 6/2005 | Meade et al. |
| 2005/0125075 A1 | 6/2005 | Meade et al. |
| 2005/0149114 A1 | 7/2005 | Cartledge et al. |
| 2005/0171556 A1 | 8/2005 | Murphy |
| 2005/0192614 A1 | 9/2005 | Binmoeller |
| 2005/0216040 A1 | 9/2005 | Gertner et al. |
| 2005/0216042 A1 | 9/2005 | Gertner |
| 2005/0228415 A1 | 10/2005 | Gertner |
| 2005/0228504 A1 | 10/2005 | Demarais |
| 2005/0240279 A1 | 10/2005 | Kagan et al. |
| 2005/0256587 A1 | 11/2005 | Egan |
| 2005/0267405 A1 | 12/2005 | Shah |
| 2005/0267499 A1 | 12/2005 | Stack et al. |
| 2005/0267533 A1 | 12/2005 | Gertner |
| 2006/0009858 A1 | 1/2006 | Levine et al. |
| 2006/0064120 A1 | 3/2006 | Levine et al. |
| 2006/0106332 A1 | 5/2006 | Knudson et al. |
| 2006/0155312 A1 | 7/2006 | Levine et al. |
| 2006/0161139 A1 | 7/2006 | Levine et al. |
| 2006/0161172 A1 | 7/2006 | Levine et al. |
| 2006/0161187 A1 | 7/2006 | Levine et al. |
| 2006/0161265 A1 | 7/2006 | Levine et al. |
| 2006/0212042 A1 | 9/2006 | Lamport et al. |
| 2006/0265082 A1 | 11/2006 | Meade et al. |
| 2006/0271175 A1 | 11/2006 | Woolfson et al. |
| 2006/0287734 A1 | 12/2006 | Stack et al. |
| 2007/0005147 A1 | 1/2007 | Levine et al. |
| 2007/0010864 A1 | 1/2007 | Dann et al. |
| 2007/0027548 A1 | 2/2007 | Levine et al. |
| 2007/0032879 A1 | 2/2007 | Levine et al. |
| 2007/0049801 A1 | 3/2007 | Lamport et al. |
| 2007/0083271 A1 | 4/2007 | Levine et al. |
| 2007/0282453 A1 | 12/2007 | Weitzner et al. |
| 2007/0293885 A1 | 12/2007 | Binmoeller |
| 2008/0071383 A1 | 3/2008 | Levine et al. |
| 2008/0097466 A1 | 4/2008 | Levine et al. |
| 2008/0103604 A1 | 5/2008 | Levine et al. |
| 2008/0208239 A1 | 8/2008 | Annunziata |
| 2008/0208357 A1 | 8/2008 | Melanson et al. |
| 2008/0223476 A1 | 9/2008 | Stinson |
| 2008/0234834 A1 | 9/2008 | Meade et al. |
| 2009/0177215 A1 | 7/2009 | Stack et al. |

FOREIGN PATENT DOCUMENTS

| | | |
|---|---|---|
| EP | 0 857 471 A2 | 8/1998 |
| EP | 0935977 A2 | 8/1999 |
| EP | 0935977 A3 | 8/1999 |
| EP | 1481649 A1 | 12/2004 |
| EP | 1 504 778 A2 | 3/2005 |
| EP | 1 504 778 A3 | 3/2005 |
| WO | WO 92/06734 | 4/1992 |
| WO | WO 95/05132 A | 2/1995 |
| WO | WO 97/03624 | 2/1997 |
| WO | WO 98/22045 A | 5/1998 |
| WO | WO 99/23953 A | 5/1999 |
| WO | WO 99/44536 A | 9/1999 |
| WO | WO 00/32137 | 6/2000 |
| WO | WO 00/42945 | 7/2000 |
| WO | WO 01/12256 A1 | 2/2001 |
| WO | WO 01/35861 A1 | 5/2001 |
| WO | WO 02/081019 A1 | 10/2002 |
| WO | WO 02/096327 A2 | 12/2002 |
| WO | WO 03/017882 A2 | 3/2003 |
| WO | WO 03/086246 A1 | 10/2003 |
| WO | WO 03/086247 A1 | 10/2003 |
| WO | WO 2004/000169 A1 | 12/2003 |
| WO | WO 2004/004542 A2 | 1/2004 |
| WO | WO 2004/004542 A3 | 1/2004 |
| WO | WO 2004/014237 A1 | 2/2004 |
| WO | WO 2004/019765 A2 | 3/2004 |
| WO | WO 2004/019765 A3 | 3/2004 |
| WO | WO 2004/021894 A1 | 3/2004 |
| WO | WO 2004/037064 A2 | 5/2004 |
| WO | WO 2004/037064 A3 | 5/2004 |
| WO | WO 2004/049982 A2 | 6/2004 |
| WO | WO 2004/064682 A1 | 8/2004 |
| WO | WO 2004/069332 A1 | 8/2004 |
| WO | WO 2004/073782 A1 | 9/2004 |
| WO | WO 2004/080336 A2 | 9/2004 |
| WO | WO 2004/087014 A2 | 10/2004 |
| WO | WO 2004/087233 A2 | 10/2004 |
| WO | WO 2004/093639 A2 | 11/2004 |
| WO | WO 2004/093639 A3 | 11/2004 |
| WO | WO 2005/011533 A1 | 2/2005 |
| WO | WO 2005/060869 A1 | 7/2005 |
| WO | WO 2005/060882 A1 | 7/2005 |
| WO | WO 2005/082296 A1 | 9/2005 |
| WO | WO 2005/110280 A2 | 11/2005 |
| WO | WO 2005/110280 A3 | 11/2005 |
| WO | WO 2005/117716 A2 | 12/2005 |
| WO | WO 2005/118049 A1 | 12/2005 |
| WO | WO 2005/120363 A1 | 12/2005 |
| WO | WO 2006/088578 A1 | 1/2006 |
| WO | WO 2006/016894 A1 | 2/2006 |
| WO | WO 2006/034062 A1 | 3/2006 |
| WO | WO 2006/078781 A1 | 7/2006 |
| WO | WO 2006/078927 A1 | 7/2006 |
| WO | WO 2006/102012 A1 | 9/2006 |

| | | | |
|---|---|---|---|
| WO | WO 2006/133311 A2 | 12/2006 | |

OTHER PUBLICATIONS

Hwang, J.C., et al., "Covered Retrievable Tracheobronichial Hinged Stent: An Experimental Study in Dogs," *J. Vasc. Interv. Radiol.*, 12(12):1429-1436 (Dec. 2001).

Irie, T., et al., "Relocatable Gianturco Expandable Metallic Stents[1]," *Radiology*, 178:575-578 (1991).

Lee, B.H., et al., "New Self-Expandable Spiral Metallic Stent: Preliminary clinical Evaluation in Malignant Biliary Obstruction," *J. Vasc Interv Radiol.*, 6(4):635-640 (Jul.-Aug. 1995).

Lee, S.H., "The Role of Oesophageal Stenting in the Non-Surgical Management of Oesophageal Strictures," *British J. Radiology*, 74:891-900 (Oct. 2001).

Shim, C.S., et al., "Fixation of a Modified Covered Esophageal Stent: Its Clinical Usefulness for Preventing Stent Migration," *Endoscopy*, 33(10):843-848 (Oct. 2001).

Song, H.Y., et al., "Benign and Malignant Esophageal Strictures: Treatment with a Polyurethane-Covered Retrievable Expandable Metallic Stent[1]," *Radiology*, 203(3):747-752 (Jun. 1997).

Song, H.Y., et al., "Covered Retrievable Expandable Nitinol Stents in Patients with Benign Esophageal Strictures: Initial Experience[1]," *Radiology*, 217:551-557 (Nov. 2000).

Song, H.Y., et al., "Tracheobronchial Strictures: Treatment with a Polyurethane-Covered Retrievable Expandable Nitinol Stent—Initial Experience," *Radiology*, 213:905-912 (Dec. 1999).

Yoon, C.J., et al., "Removal of Retrievable Esophageal and Gastrointestinal Stents: Experience in 113 Patients," *American J. of Roentgenology*, 183:1437-1444 (Nov. 2004).

Rubino, F., et al., "Potential of Surgery for Curing Type 2 Diabetes Mellitus," *Annals of Surgery*, 236(5):554-559 (2002).

Rubino, F. and J. Marescaux, "Effect of Duodenal-Jejunal Exclusion in a Non-obese Animal Model of Type 2 Diabetes, A New Perspective for an Old Disease," *Annals of Surgery* 239(1):1-11, Jan. 2004.

\* cited by examiner

FIGURE 4A
FIGURE 4B
FIGURE 4C
FIGURE 4D

Piston Closed

Piston Open

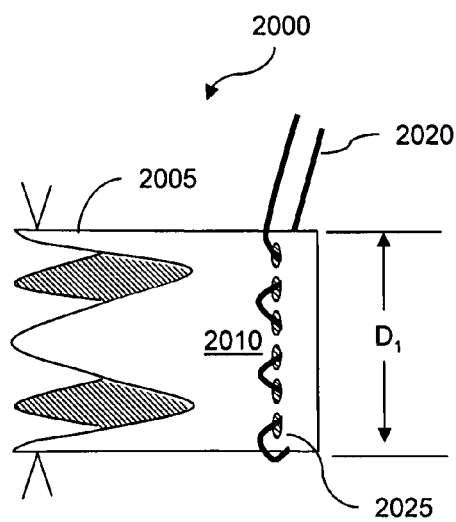
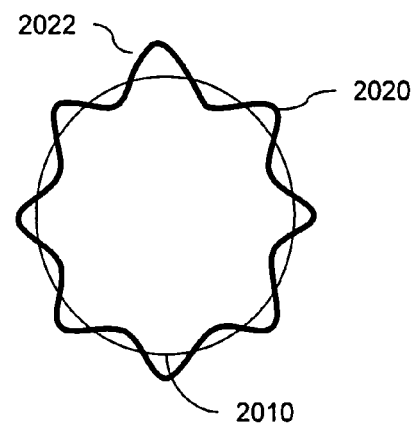
FIG. 20A
FIG. 20B
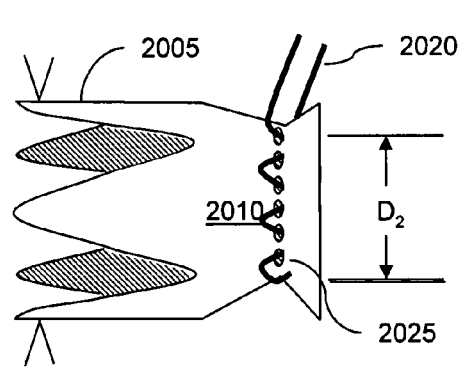
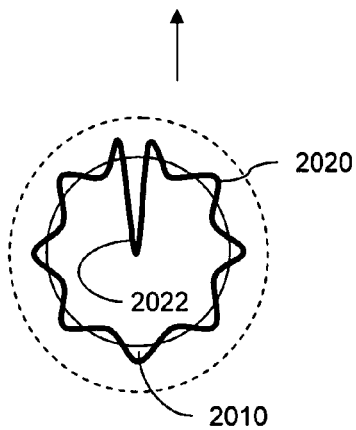
FIG. 20C
FIG. 20D

RESISTIVE ANTI-OBESITY DEVICES

RELATED APPLICATIONS

This application is a continuation of U.S. application Ser. No. 11/821,551, filed on Jun. 22, 2007, now abandoned which claims the benefit of U.S. Provisional Application No. 60/816,143, filed on Jun. 23, 2006. The entire teachings of the above applications are incorporated herein by reference.

BACKGROUND OF THE INVENTION

According to the Center for Disease Control (CDC), over sixty percent of the United States population is overweight, and almost twenty percent are obese. This translates into 38.8 million adults in the United States with a Body Mass Index (BMI) of 30 or above. The BMI is defined as a person's weight (in kilograms) divided by height (in meters), squared. To be considered clinically, morbidly obese, one must meet one of three criteria: BMI over 35, 100 pounds overweight, or 100% above ideal body weight. There is also a category for the super-obese for those weighing over 350 pounds.

Obesity is an overwhelming health problem. Because of the enormous strain associated with carrying this excess weight, organs are affected, as are the nervous and circulatory systems. In 2000, the National Institute of Diabetes, Digestive, and Kidney Diseases (NIDDK) estimated that there were 280,000 deaths directly related to obesity. The NIDDK further estimated that the direct cost of healthcare in the U.S. associated with obesity is $51 billion. In addition, Americans spend $33 billion per year on weight loss products. In spite of this economic cost and consumer commitment, the prevalence of obesity continues to rise at alarming rates. From 1991 to 2000, obesity in the U.S. grew by 61%. Not exclusively a U.S. problem, worldwide obesity ranges are also increasing dramatically.

One of the principle costs to the healthcare system stems from the co-morbidities associated with obesity. Type-2 diabetes has climbed to 7.3% of the population. Of those persons with Type-2 diabetes, almost half are clinically obese, and two thirds are approaching obese. Other co-morbidities include hypertension, coronary artery disease, hypercholesteremia, sleep apnea and pulmonary hypertension.

Although the physiology and psychology of obesity are complex, the medical consensus is that the cause is quite simple—an over intake of calories combined with a reduction in energy expenditures seen in modern society. While the treatment seems quite intuitive, the institution of a cure is a complex issue that has so far vexed the best efforts of medical science. Dieting is not an adequate long-term solution for most people. Once an individual has slipped past the BMI of 30, significant changes in lifestyle are the only solution.

There have been many attempts in the past to surgically modify patients' anatomies to attack the consumption problem by reducing the desire to eat. Stomach staplings, or gastroplasties, to reduce the volumetric size of the stomach, thereby achieving faster satiety, were performed in the 1980's and early 1990's. Although able to achieve early weight loss, sustained reduction was not obtained. The reasons are not all known, but are believed related to several factors. One of which is that the stomach stretches over time increasing volume while psychological drivers motivate patients to find creative approaches to literally eat around the smaller pouch.

Surgeries can generally be separated into restrictive procedures, malabsorptive procedures and combinations thereof. At least two surgical procedures that successfully produce long-term weight loss are the Roux-en-Y gastric bypass, and the biliopancreatic diversion with duodenal switch (BPD). Both procedures reduce the size of the stomach plus shorten the effective-length of intestine available for nutrient absorption. Reduction of the stomach size reduces stomach capacity and the ability of the patient to take in food. Bypassing the duodenum makes it more difficult to digest fats, high sugar and carbohydrate rich foods.

The Laparoscopic Adjustable Gastric Band is a device that is placed around the top of the stomach to create a restriction. This forces the patient to eat smaller meals as the food must pass from the small pouch into the rest of the stomach before he/she can eat again. This device however does require surgery for its placement and is difficult to remove.

These procedures carry a heavy toll. The morbidity rate for bariatric surgical procedures is alarmingly high with 11% requiring surgical intervention for correction. Early small bowel obstruction occurs at a rate of between 2-6% in these surgeries and mortality rates are reported to be approximately 0.5-1.5%. While surgery is effective, the current invasive procedures are not acceptable with these complication rates. Laparoscopic techniques applied to these surgeries result in fewer surgical complications but continue to expose these very ill patients to high operative risk in addition to requiring an enormous level of skill by the surgeon.

Devices to reduce absorption in the small intestines have been proposed (see U.S. Pat. No. 5,820,584 (Crabb), U.S. Pat. No. 5,306,300 (Berry) and U.S. Pat. No. 4,315,509 (Smit)). Restrictive devices include Laparoscopic Adjustable Gastric Banding (LABG) (see for example U.S. Pat. No. 5,226,429 (Kuzmak)) and gastric balloons (see for example U.S. Pat. No. 4,823,808 (Clegg et al.) and U.S. Pat. No. 6,755,869 (Geitz)).

SUMMARY OF THE INVENTION

The present invention relates to methods, devices and systems that provide an increased sense of satiety to a person by increasing the resistance to the outflow of food from the stomach. Gastric emptying can be slowed using devices that slow the passage of chyme through the proximal portion of the intestines or through the pylorus. Slowing gastric emptying may induce satiety for a longer than normal period and may therefore reduce food consumption. Although many of these concepts include intestinal sleeves, they need not. The resistor concept may be applied to a simple anchor and resistor without a long sleeve. Gastrointestinal devices with resistors are further described in U.S. application Ser. No. 11/330,705, filed Jan. 11, 2006, which claims the benefit of U.S. Provisional Application No. 60/662,570, filed on Mar. 17, 2005, herein incorporated by reference in their entireties.

Restrictive devices have been previously described but most commonly are described to reside within the stomach, the esophagus and the gastro-esophageal junction. Anchoring devices in the stomach is difficult as the stomach is a particularly active region of the anatomy tending to tear out devices implanted therein. The devices described herein are more typically anchored in the intestines.

The current device is a gastrointestinal implant that includes an anchor adapted to be retained within the pyloric orifice or distal to the pylorus. The implant further includes a restricting aperture attached to the anchor that retards the outflow of food from the stomach In one embodiment, the aperture is elastic and expandable under pressure from material flowing through the anchor and the aperture at elevated physiological pressures. The aperture ranges in diameter from 1 to 10 millimeters over a range of water pressure. The aperture expands substantially at a physiological pressure of 50 inches of water or more. The diameter of the aperture is about 5 mm or below, and is preferably about 4 mm or below when the water pressure is between 0 inches and 50 inches of water. The diameter of the aperture opens to greater than 4 mm when the water pressure is above 50 inches of water. The aperture is made of a biocompatible material such as silicone.

The device may also include a flexible and floppy sleeve material that is adapted to connect the flexible aperture to the anchor and that is adapted to encapsulate the anchor and the aperture. The aperture may therefore, be within the sleeve material.

The implant can also include a flexible, floppy sleeve that is at least one foot in length to extend into the intestine. The proximal end of the sleeve is attached to the anchor. The sleeve extends into the intestine and defines a lumen through which chyme passes. The implant further includes a restricting aperture within the sleeve, wherein the aperture is adapted to retard the outflow of food from the stomach.

Further, a method of treating obesity includes implanting a device within a gastrointestinal tract of an animal at or distal to the pylorus, with the implanted device, resisting the outflow of food from the stomach with a restrictive aperture.

An additional method of treating obesity includes anchoring a flexible, floppy sleeve with an anchor in the intestine, wherein the sleeve extends into the intestine, and further restricting the outflow of food from the stomach with a restrictive aperture within the sleeve.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIGS. 4A-4D are end views showing alternative types of restrictive members used in the embodiment of the invention shown in FIG. 3;

FIG. 20A-20D are schematic diagrams illustrating side views of an embodiment of the invention including a drawstring restrictor shown in the open and partially-closed positions, respectively.

DETAILED DESCRIPTION OF THE INVENTION

A description of preferred embodiments of the invention follows.

This general concept relates to providing an increased sense of satiety by slowing gastric emptying by providing resistance to the outflow of food from the stomach and through the intestines. An increased sense of satiety is obtained by slowing emptying of an animal's stomach. Gastric emptying can be slowed by providing resistance to the outflow of food, or chyme, from the stomach. In general, an animal perceives a sensation of satiety when the stomach fills. It is believed that by slowing gastric emptying into the duodenum, an animal can maintain a feeling of satiety for a longer period of time. Consequently, an animal no longer feeling hungry will tend to eat less.

A restrictor within the intestine slows the flow of gastric contents by creating an artificial, non-permanent narrowing in the gastrointestinal tract. Delayed emptying of chyme through the gastrointestinal tract will create both a premature feeling of satiety during meals and a lasting feeling of satiety after meals.

A resistive implant is preferably placed at a predetermined location within the body and adapted to remain there throughout a course of treatment. To maintain the implant in place, at least a portion of the device is secured to the surrounding anatomy. Securing an implant can be accomplished using an anchor coupled to the device. Anchoring within the gastrointestinal tract, however, poses numerous challenges due at least in part to the physiology of the anatomical region, its high degree of motility, and pressures resulting from digestive forces.

One region of the gastrointestinal tract that is particularly well suited for anchoring the resistive implant is the proximal duodenum. Compared to the stomach, the pylorus, and even distal regions of the small intestine, the proximal duodenum is relatively immotile. Additionally, the proximal duodenum defines a slightly enlarged cavity just distal to the pyloric sphincter, referred to as the duodenal bulb. An anchor of the type shown in FIG. 1A that expands to conform to the lumen is particularly well suited for positioning within the bulbous duodenum. The shape of the cavity and its relatively low motility will enhance performance of the anchoring device.

Figure 1B:
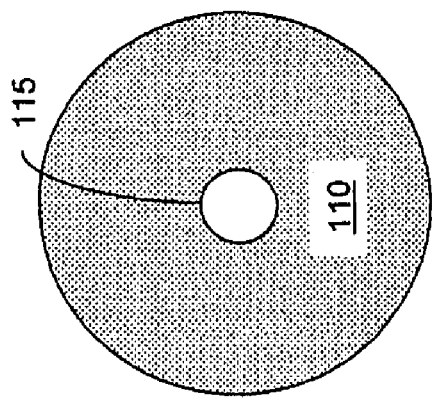
FIG. 1B is a schematic diagram of an end view of the embodiment of FIG. 1A.
Figure 1A:
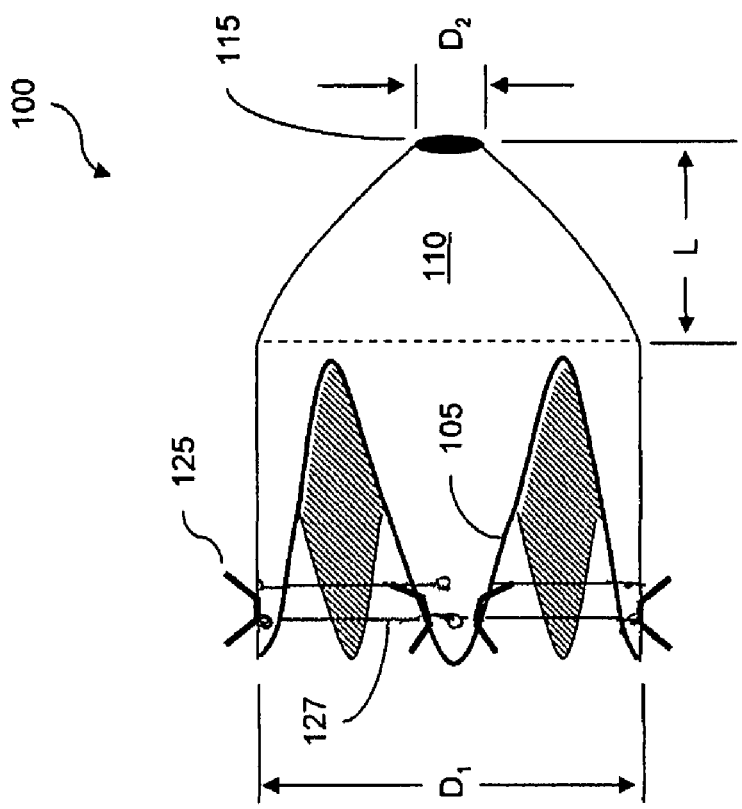
FIG. 1A is a schematic diagram illustrating a side view of the embodiment of the invention including an artificial stricture.

An exemplary artificial stricture device 100 adapted for gastrointestinal applications is illustrated in FIG. 1A. The device 100 includes an anchoring element 105 coupled to an artificial stricture. The artificial stricture retards the flow of chyme therethrough. The anchor 105 is adapted to anchor the device 100 within the gastrointestinal tract. When placed at or below the pylorus, the stricture operates to slow gastric emptying. The anchor is adapted to hold the device securely in place under gastrointestinal forces and pressures.

The anchor 105 can be a radial spring defining an opening therethrough for the passage of chyme and adapted to engage the surrounding tissue of the hollow organ within which it is implanted. Thus, the anchor 105 can provide an interference fit to the surrounding tissue. In some embodiments, the perimeter of the anchor 105 is in sealable communication with the surrounding tissue of the lumen to prevent leakage of chyme and fluids beyond the artificial stricture.

Referring again to FIG. 1A, the anchor 105 generally defines a central lumen through which chyme flows. The anchor can include a stent, such as the stents described in U.S. Pat. No. 7,025,791, issued Apr. 11, 2006, incorporated herein by reference in its entirety. Alternatively or in addition, the anchor 105 can include a radial spring, such as the wave anchor illustrated and described in more detail in U.S. patent application Ser. No. 10/858,851, filed on Jun. 1, 2004, which claimed priority to U.S. Provisional Application Ser. No. 60/544,527, filed on Feb. 13, 2004, and U.S. Provisional Application Ser. No. 60/528,084, filed on Dec. 9, 2003, incorporated herein by reference in its entirety.

The anchor 105 can attach to the intestine using a frictional or interference fit. Thus, the anchor 105 can have a relaxed diameter that is greater than the maximum anticipated diameter of the intestine, such that the anchor 105 will provide an outward force against the adjacent anatomy, acting to keep the anchor 105 in place.

Alternatively or in addition, the anchor 105 can include one or more external barbs 125 further securing the implant device in the presence of peristalsis. Preferably, the barbs 125 are sized and positioned to engage muscular tissue. Exemplary barbs are described in more detail in U.S. Pat. No. 7,080,849, issued Jul. 25, 2006, and U.S. patent application Ser. No. 10/858,852, filed on Jun. 1, 2004, which claimed priority to U.S. Provisional Application Ser. No. 60/544,527, filed on Feb. 13, 2004, and U.S. Provisional Application Ser. No. 60/528,084, filed on Dec. 9, 2003, incorporated herein by reference in their entirety.

The anchor 105 can also include one or more repositioning features. As shown the device includes a drawstring 127 at its proximal end. The drawstring 127 is threaded through the open end of the anchor 105 such that it can be grasped and used to facilitate repositioning of the anchor 105 within the body or removal of the anchor 105 from the body. Removal methods and devices using a drawstring are described in U.S. application Ser. No. 11/318,083, entitled "Removal and Repositioning Device" filed on Dec. 22, 2005 and incorporated herein by reference in its entirety.

The artificial stricture can be formed from a blocking material 110 coupled to the anchor 105, the blocking material defining the aperture 115 therein. The blocking material is dimensioned to at least cover the cross-sectional area of the lumen within which it is implanted. For an implant adapted for use in the proximal duodenum of an adult male, the diameter of the impermeable material would be at least about 25 millimeters.

The blocking material 110 may be constructed of a compliant or non-compliant polymer. If non-compliant, such as 0.0005" thick ePTFE and FEP, then the hole size remains fixed and also can be dilated with a balloon as it will plastically deform. If compliant, such as with 0.015" thick, lower durometer silicone that is preferably below 30A, the hole may enlarge in response to elevated pressures that result when the hole gets obstructed by large food particles. The blocking material 110 can alternatively or in addition be made of the same material described in more detail below in the reference to intestinal sleeves.

In some embodiments, the anchor 105 is attached to a material similar to the blocking material. For example, the anchor 105 can be encapsulated between overlapping layers of a tubular segment of blocking material. The blocking material 110 defining the aperture 115 can then be formed in the same blocking material that is attached to the anchor 105. Alternatively, a different blocking material 110 can be used.

The blocking material 110 can first be formed into a suitable pattern, such as the circle shown and then attached to the anchor and/or to material covering the anchor 105. When the anchor 105 is also attached to the blocking material, the different segments of blocking material 110 can be sealably attached together using any suitable means. For example, the blocking material 110 can be attached to the anchor covering by suturing. Alternatively or in addition, the blocking material 110 can be attached to the anchor covering by a chemical fastener, such as an adhesive, and/or by thermal bonding. Formed in this manner, the attached blocking material 110 may extend for some distance L from the distal end of the anchor 105 when in the presence of a proximal pressure (e.g., the material bulges out in an elongated or domed fashion). In some embodiments, the blocking material 110 is attached in a relatively taught manner, similar to the skin of a drum to limit any axial extent L of the blocking material 110 beyond the distal end of the anchor 105.

The stricture is created by forming an aperture 115 having a reduced cross-sectional area, or diameter within the blocking material 110. The aperture can be formed, for example, by simply cutting or punching a hole of the appropriate dimensions into the blocking material 110. For example, the hole can be less than about 10 millimeters in diameter for an exemplary 25 millimeter implant. In some embodiments, the aperture is about 5 millimeters in diameter or less. It is unlikely, however, that an aperture of less than about 2 millimeters would be used in a human application as food particle passing through the pylorus are typically about 1-2 millimeters or less in size.

Figure 7:
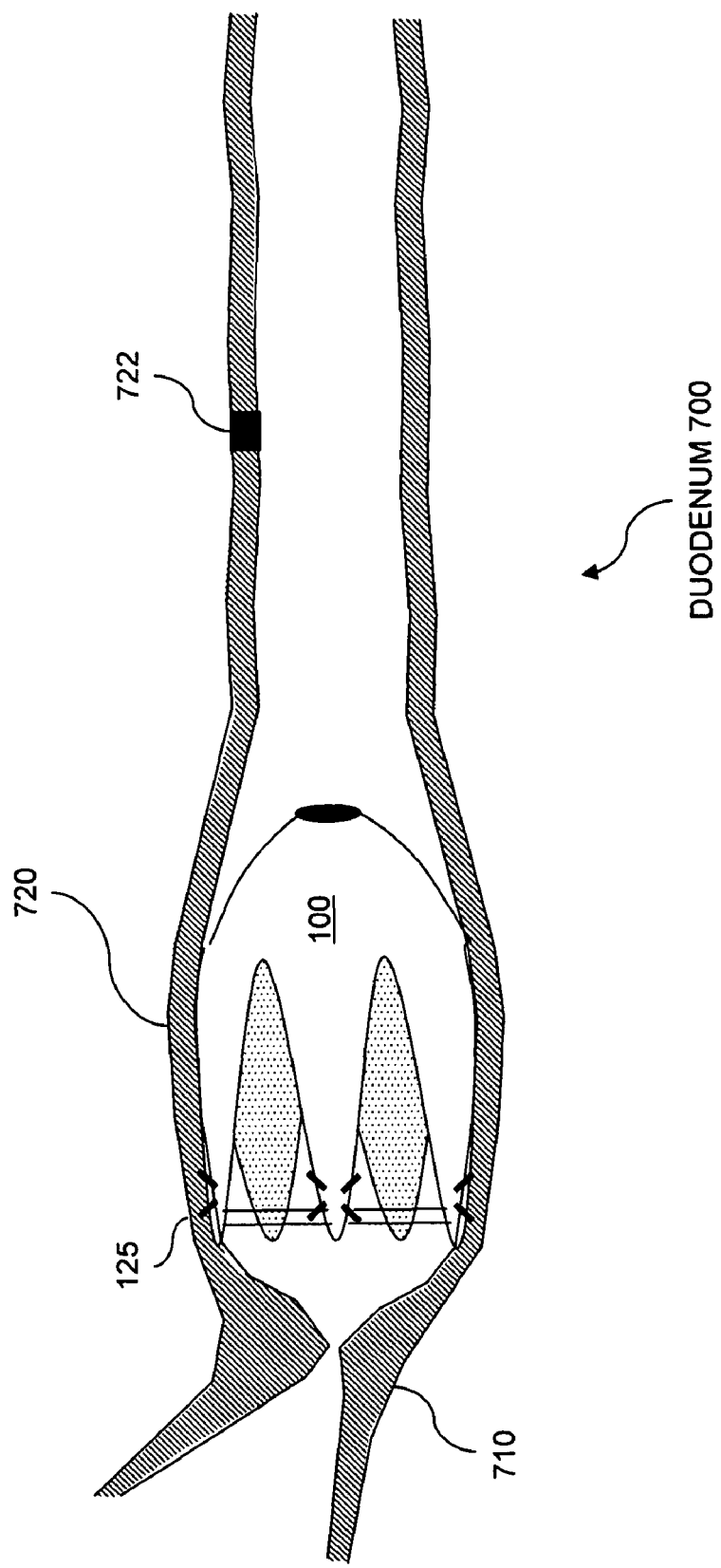
FIG. 7 is a schematic diagram illustrating the artificial structure of FIG. 1A implanted within the proximal duodenum.

A cross section of a proximal duodenum including an artificial stricture 100 (FIG. 1A) implanted therein, is illustrated in FIG. 7. The stricture is positioned distal to the pylorus 710 and proximal to the ampulla of vater 722, in the duodenal bulb 720. The stricture 100 includes barbs 125 that are sized to engage muscular tissue of the intestine. The radial expansive force of the anchor maintains the proximal end of the stricture 100 sealably engaged with the interior walls of the duodenal bulb 720. The radial force is also sufficient to keep the barbs 125 firmly implanted within the surrounding tissue. Chyme emptying into the duodenum 700 through the pylorus 720 encounters the artificial stricture 100. The reduced aperture of the stricture decreases the rate at which chyme passes into the distal duodenum 700. As chyme continues to empty from the stomach, the chyme builds up along a proximal side of the stricture 100. Thus, the stomach empties at a slower rate than would otherwise occur without the stricture due to the reduced aperture of the stricture 100. Exemplary fluid flow rates can be 2 cm/sec through a 25 mm diameter opening.

Positioning the implant 700 in the pyloric orifice or distal to the pylorus is advantageous in achieving greater weight loss than a device anchored in the upper gastrointestinal tract. For example, if a restrictive implant is anchored in the esophageal area, a restrictive orifice would have a larger diameter than one in the pyloric area as food would need to pass through as opposed to only chyme. This allows a patient to still ingest heavier liquefied food and drinks without restriction (for example milk shakes and other heavier liquefied foods) as the density of the liquid allows it to pass through the larger aperture. This would in turn, not result in increased weight loss. If the smaller restrictive aperture is in the pyloric area however, any food (including fatty liquefied foods) is broken down into a chyme that is restricted at the same rate regardless of what the initial food was, thus resulting in increased weight loss. Additionally, if a patient with a restrictive implant in the esophageal area overeats, the food will backup and potentially cause sickness or vomiting. If one overeats with a pyloric restrictive implant, the backup of chyme will tend to cause a feeling of increased satiety and not sickness.

Figure 2:
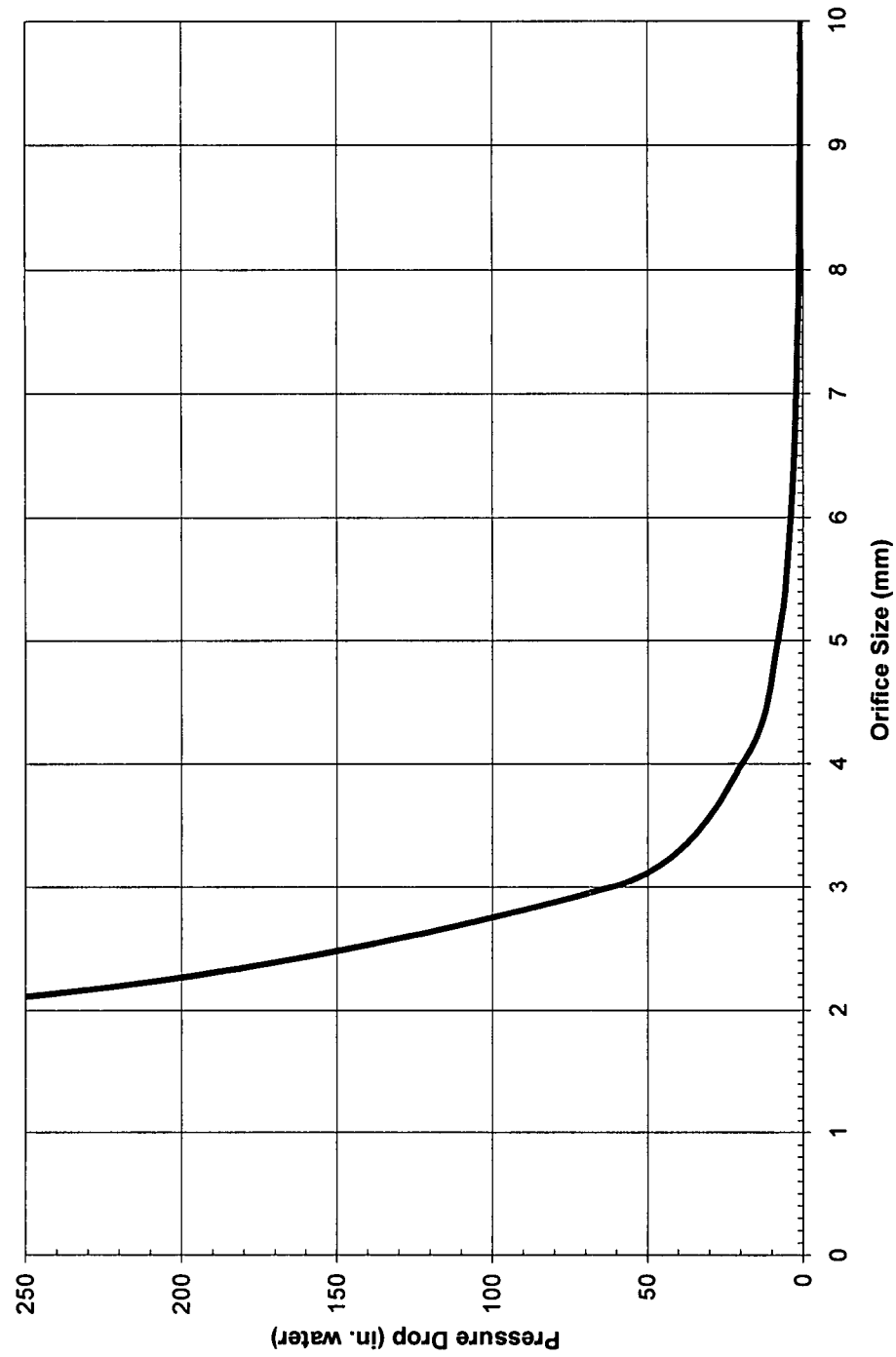
FIG. 2 is a graph illustrating the pressure drop of an exemplary fluid through an aperture of varying size.

Fluid mechanics can be used to determine the size aperture needed to provide a restriction within the duodenum. For example, the Bernoulli equation can be applied to the flow of a Newtonian fluid through an aperture as provided in equation 1. In this equation, $\Delta P$ represents the pressure drop across the aperture, $\rho$ corresponds to the fluid density, Q corresponds to the volume flow (determined as the product of the fluid velocity and the flow area), D is the diameter of the unobstructed opening (e.g., about 25 mm in the example of FIG. 2), and d is the diameter of the aperture in millimeters. In the example of FIG. 2, the diameter of the aperture is varied between about 2 and 10 mm.

$$\Delta P = (8\rho Q^2)/(\pi^2 D^4) * [(D/d)^4 - 1] \quad (1)$$

An exemplary graph of the pressure drop through an aperture of varying size is provided in FIG. 2. The graph was determined by applying equation 1 using an assumed velocity of about 2 cm/sec, which corresponds to the mean flow rate of chyme through the intestines. Considering peristaltic pressures on the order of 20-40 inches of water (an exemplary range of pressures corresponding to the chyme flow of an adult human), the aperture size should be less than about 5 mm in diameter to provide flow resistance. More preferably, the aperture size is less than 5 mm. For example, an aperture of about 3 mm provides increased flow resistance under nominal anticipated peristaltic pressures.

Figure 17:
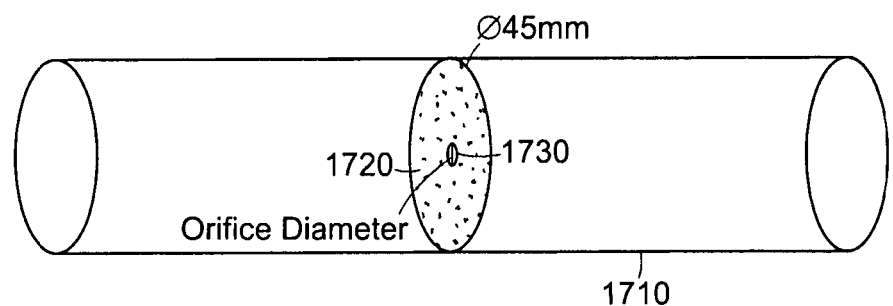
FIG. 17 shows a model of the gastrointestinal tract and aperture within the tract.

A study was conducted to model and analyze the back pressure required to maintain a steady flow of chyme through an aperture. In order to analyze the pressure drop across the aperture, numerous simplifications and assumptions were required. The model is shown in FIG. 17. First, the duodenum was modeled as a rigid, straight tube 1710 with an inner diameter of 45 mm. The diameter measurement is based on previous animal experience that has shown in-vivo anchor diameters of roughly 45 mm after 3 weeks of implant.

A plate type restrictor 1720 was modeled as a rigid disk with outer diameter of 45 mm, such that it fits line-to-line within the rigid tube model of the duodenum. The plate was assumed to have a theoretical width of zero and was placed at the midpoint of the duodenum tube 1710. The plate restrictor 1720 has an aperture 1730 within it. The aperture diameter 1730 was varied from 1 mm to 10 mm with the associated pressure drops tabulated.

The following conditions were assumed for the test:
Steady flow of chyme
Incompressible flow of chyme
Frictionless flow of chyme
Flow along a streamline within the duodenum
Density of chyme~density of water, $\rho = 1000$ kg/m³
Flow rate of chyme through intestines, $Q = 3.9 \times 10^{-5}$ m³/s–>v=2 cm/s The pressure at the proximal side of the duodenum required to maintain a steady flow rate of $3.9 \times 10-5$ m³/s through the aperture 1730 is calculated by applying the Bernoulli equation along a streamline:

$$p_{1g} = p_1 - p_{atm} = p_1 - p_2 = \frac{\rho}{2}(V_2^2 - V_1^2) = \frac{\rho}{2}V_1^2\left[\left(\frac{V_2}{V_1}\right)^2 - 1\right]$$

Applying the continuity equation and replacing Areas with Diameters yields:

$$p_{1g} = \frac{8\rho Q^2}{\pi^2 D_1^4}\left[\left(\frac{D_1}{D_2}\right)^4 - 1\right]$$

Figure 18:
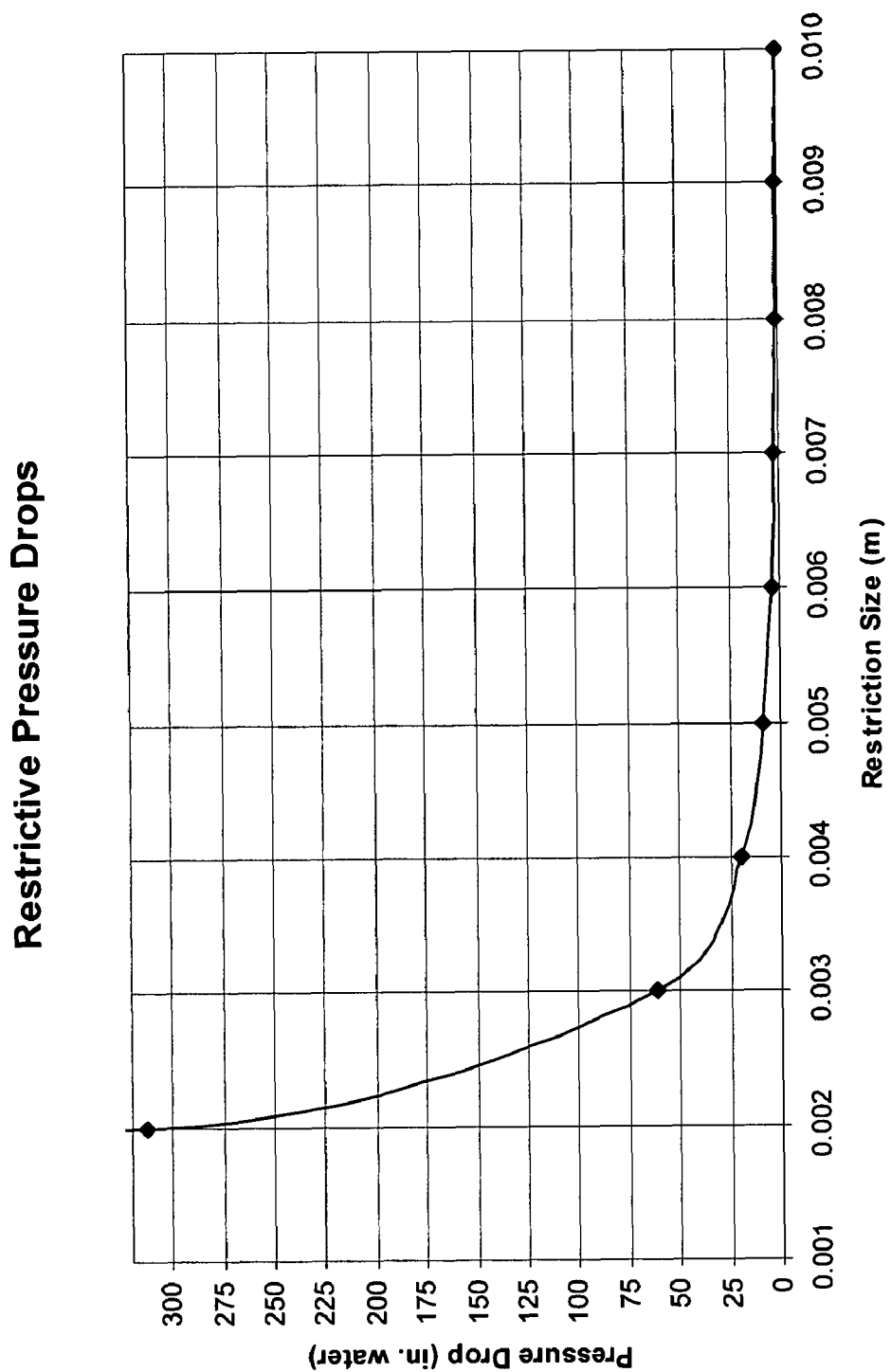
FIG. 18 shows a model pressure drop curve for one type of restrictor.

Based on this study, the chart in FIG. 18 shows the back pressure required for each aperture diameter from 1 mm to 10 mm. This analysis suggests that a restriction of at least 5 mm will be required to achieve a significant increase in back pressure. The pressure requirement and therefore restrictive effect increases dramatically from 5 to 3 mm. Below 3 mm, the back pressure requirement exceeds anatomical capabilities. This model therefore predicts that the plate restrictor design will be most effective in the 3-5 mm range.

In some embodiments, the aperture is adjustable. For example, an aperture can be increased by stretching it until the blocking material defining the aperture plastically deforms to a new, larger diameter. Stretching can be accomplished using a balloon inserted into the aperture, the balloon being inflated after insertion. The pressure of the inflated balloon will stretch a suitable blocking material to a larger size. When the balloon is removed, the material will retain the enlarged aperture.

Thus, the diameter of the aperture can be adjusted to selectably increase and/or decrease its diameter. Varying the diameter of the aperture similarly affects the resistance offered by the device to the flow of chyme therethrough and can be advantageous for tailoring performance of the device during a particular course of treatment. For example, if a patient outfitted with an adjustable device is not losing weight sufficiently, the diameter of the aperture can be altered to vary the performance (i.e., the aperture can be narrowed to provide more restriction, ideally leading to greater weight loss). Preferably, adjustments to the aperture can be accomplished remotely or using an endoscopic procedure and without the need for surgery. Alternatively or in addition, adjustment can be accomplished through a remote, subcutaneous route.

An exemplary embodiment of an artificial stricture having an adjustable orifice is illustrated in FIGS. 20A through 20D. An intestinal implant 2000 includes an anchor 2005 coupled to a length of a sleeve 2010. At least a portion of the sleeve is altered to form an adjustable orifice or restriction. As shown, the sleeve 2010 can be altered using a drawstring 2020. For example, the implant 2000 includes a collapsible lumen and a drawstring. The collapsible lumen is operable by adjusting the drawstring 2020 to selectively change the size of a constriction within the lumen. Thus, the drawstring can be used to alter the size of the orifice between an unconstrained diameter $D_1$ (FIG. 20A) and a reduced diameter $D_2$ (FIG. 20C). In some embodiments, the drawstring 2020 is provided at a distal end of a relatively short gastrointestinal sleeve 2010, as shown. Alternatively, the sleeve 2010 may extend for a predetermined length and the drawstring 2020 positioned at any preferred location along the length of the sleeve 2010.

The drawstring 2020 can be sewn into the sleeve 2010 in a purse string fashion, as shown. That is, the drawstring can be laced through holes or eyelets 2025 formed in the sleeve material and extending about the perimeter of the sleeve 2010 (FIG. 20B). Alternatively or in addition, the drawstring 2020 can be inserted into a hem or a casing, provided within the sleeve 2010 (not shown). Usually, when using a hem or a casing at least one access port will be necessary through which the drawstring can be grasped for adjustment.

In some embodiments, the drawstring 2020 includes at least one feature adapted for grasping. For example, the drawstring 2020 can include at least one loop 2022 that may extend within the interior lumen of the sleeve 2010. The loop 2022 can be grasped by a device and manipulated to alter the diameter of the sleeve 2010. As shown in FIG. 20D, pulling the loop 2022 results in a reduction of the diameter of the sleeve 2010.

In yet other embodiments, the drawstring 2020 can be used to adjust the diameter of the anchor 2005 itself. For example, the drawstring 2020 can be woven through the distal end portion of an anchor 2005 (not shown), such that an adjustment of the drawstring 2020 changes the diameter of the distal end of the anchor 2005.

Once implanted, the drawstring 2020 can be accessed remotely (e.g., endoscopically). An instrument, such as a hook, or pinchers can be used to grasp an exposed portion of the drawstring. Once grasped, the drawstring 2020 can be adjusted to create a smaller or larger opening. For example, the drawstring 2020 can be pulled away from a wall of the sleeve 2010 (e.g., radially inward), in a proximal or distal direction along the length of the sleeve 2010 (e.g., axially), or in a combination of both radial and axial directions.

The drawstring 2020, once adjusted, can include a feature, such as a locking means, to retain the drawstring 2020 in the adjusted position. It should be noted that locking the drawstring 2020 holds it in place to prohibit any further unintentional adjustment (e.g., expansion) of the orifice. Preferably, the locking means is reversible such that it can be locked, unlocked, and then locked again for re-adjustment. For example the drawstring 2020 can include a mechanical clip, or more simply a knot, suitably placed to limit further adjustment. In some embodiments a knot can be provided in the drawstring 2020 to prohibit expansion of the device beyond a maximum diameter as set by placement of the knot.

In other embodiments, the blocking material of FIG. 1A is elastomeric such that the aperture is permitted to temporarily expand above certain pressures to prevent blockage of the aperture for food particles larger than the relaxed dimension the aperture returning to its reduced diameter thereafter.

In general, the small intestine tract has a native diameter of roughly 25 mm. If analyzed as a straight pipe with an inner diameter of 25 mm, very little pressure is required to propel fluids through this lumen. However, with a narrowing in the range of 0-5 mm, particularly about 4 mm or less, the pressure requirements increase dramatically. In order to slow the movement of gastric contents, a variable gastrointestinal aperture should have a steady state opening of less than 5 mm.

Figure 8A:
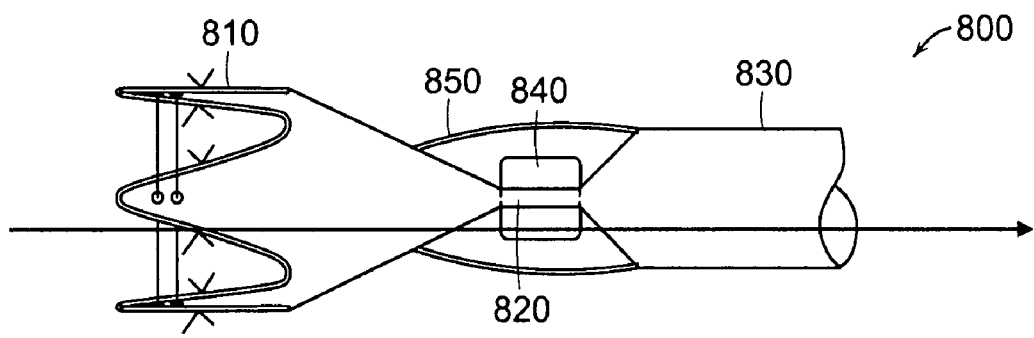
FIGS. 8A-8B illustrate an embodiment of an implantable device including an anchor coupled to an aperture.
Figure 8B:
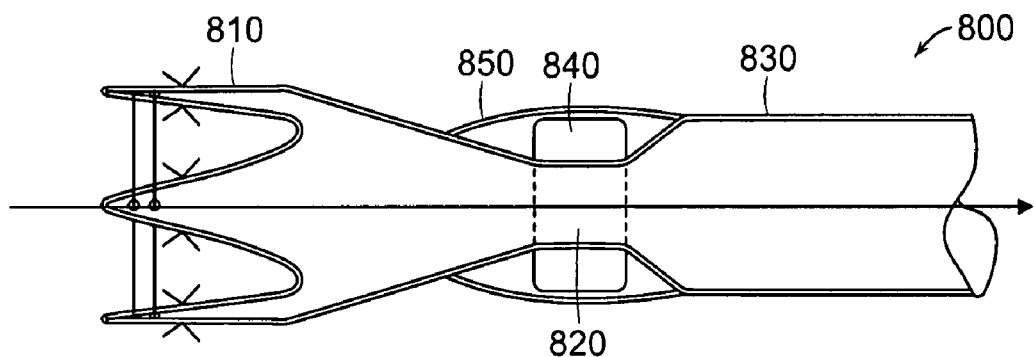

An embodiment of a variable aperture implant 800 is shown in FIGS. 8A-8B. The implant 800 includes an anchor 810 to keep the implant in place. The implant 800 also has an elastic or variable aperture 820. The variable aperture 820 creates a narrowing that restricts fluid or chyme flow from the stomach into the intestine. Surrounding the variable aperture 820 is a flexible cylinder 840. The cylinder 840 may be made of any suitable elastic biocompatible material, but is preferably made of silicone. The cylinder 840 is further covered by an outer sleeve material 850. The outer sleeve material can be formed from a fluoropolymer, preferably such as expanded polytetrafluoroethylene (ePTFE). The outer sleeve layer 850 secures the position of the flexible ring 840 and also advantageously seals it from the digestive enzymes in the intestine.

In some embodiments, the variable aperture implant 800 may further include an inner sleeve material 830 that connects the aperture 820 to the anchor 810. The inner sleeve material 830 may be made of a similar material as the outer sleeve material 850. The inner sleeve material 830 further encapsulates the anchor 810 and the aperture 820.

In operation, the variable aperture 820 expands radially under pressure to relieve blockages or excess build-up of chyme from the stomach as shown in FIG. 8B. In the relaxed stated as shown in FIG. 8A, the flexible cylinder 840 exerts pressure on the aperture 820 within the inner sleeve material 830, folding it down to a diameter significantly smaller than its unconstrained diameter; for example reduced from an expanded diameter of 10 mm down to a constrained diameter of 1 mm. In that condition, the outer sleeve material 850 is loose and baggy.

When pressure is exerted through the inner sleeve lumen 830 to a proximal edge of the flexible cylinder 840, the flexible cylinder 840 will stretch open allowing the aperture 820 within the inner sleeve material 830 to unfold to a larger diameter, or up to its maximum diameter depending on the amount of pressure exerted. In that condition, the outer sleeve material 850 stretches and becomes somewhat taut.

The design of the aperture 820 is such that this expansion can be achieved by elevated physiological pressures. Information available in the field of the art as well as an empirical data collection from a porcine model suggests that the gastrointestinal tract can normally generate pressures up to 50 inches of water. The variable aperture 820 is thus designed within the framework of creating a restriction under low pressures and opening under elevated pressures, particularly those pressures, significantly greater than 50 inches of water.

Figure 9:
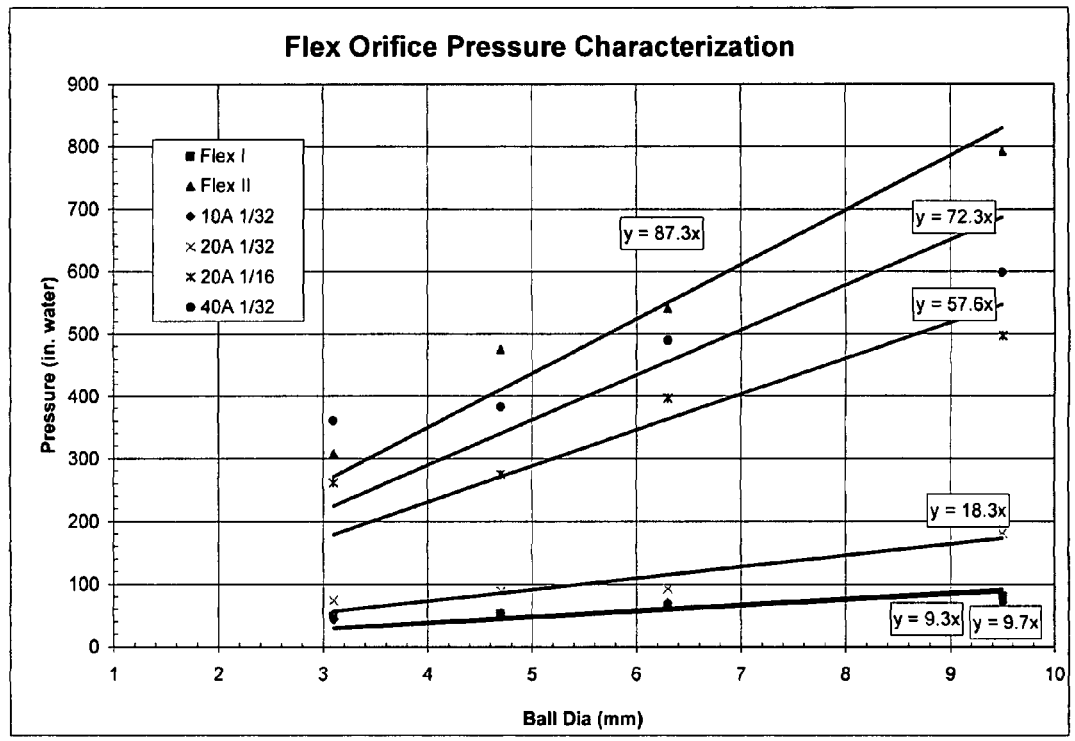
FIG. 9 illustrates the pressure characterization of different types of restrictor devices.

A compliance test was established in order to evaluate the stiffness of the variable aperture component, the results of which are show in FIG. 9. Using an Instron, gauge balls of various diameters (3-10 mm) were pulled through the variable aperture. The peak force required to pull each ball was recorded. A pressure profile for each device was then derived based on these forces and diameters. The profiles of two types of restrictors, Flex I, that is made of a lower durometer silicone and Flex II, which is made of a higher durometer silcone along with several other devices of known durometer and thickness are shown.

The Flex I restrictor has a total implant length of 4 inches inclusive of the anchor, the aperture, and the sleeve material. The variable aperture is punched into sheet of silicone rubber. The silicone is a lower durometer silicone of about 5 A. The aperture has a steady state inner diameter of about 1 mm and can expand under higher pressures to a diameter of 10 mm. The thickness of the silicone sheet is approximately 9 mm. The stead-state outer diameter of the silicone sheet is approximately 12 mm.

The Flex II type variable aperture has similar dimensions to the Flex I type aperture, except that the aperture is punched into a higher durometer silicone of 40 A.

Figure 10:
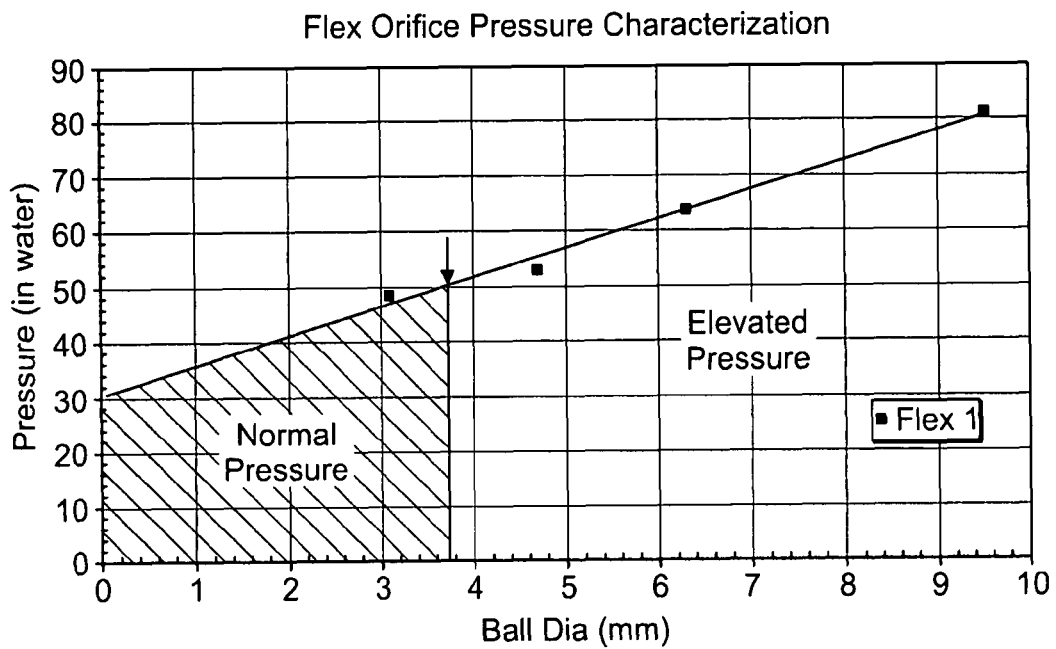
FIG. 10. illustrates the pressure characterization of one type of restrictor device.

Looking specifically at the Flex I Restrictor, the pressure curve of FIG. 10 illustrates how restriction is achieved. Duodenal manometry studies show that the pressure in the upper gastrointestinal tract varies with time as a series of high-pressure peaks. Under normal conditions, these pressure peaks are less than 50 inches of water in magnitude. The intersection of the Flex I pressure profile and this pressure is highlighted on the graph below. This intersection occurs at roughly 3.75 mm.

In other words, the aperture diameter under normal conditions is less than 4 mm, which has been shown in previous animal studies to be adequate for restriction. If the restriction becomes obstructive, the pressure in the duodenum will increase above normal levels (>50 inches of water) and the aperture will in turn expand to clear any blockages. Therefore, restriction can be achieved as with a static aperture restrictor, but without the corresponding risks of obstruction.

The variable aperture implant, therefore, raises the outlet pressure of the stomach; therefore slowing the emptying of the stomach. As previously stated, this can be achieved with a 3-4 mm fixed aperture. If however the viscosity of the chyme rises, or if the aperture gets plugged, the stomach pressure will start to rise. As it does, the variable aperture increases in diameter to maintain the pressure of the stomach close to the 50 inches of water. The variable aperture thus, is not a flapper type of valve. It is actually a pressure control device that maintains a higher pressure within the stomach. A flapper valve would open dramatically and reduce the stomach pressure. The variable aperture is more gradual in its dilation in response to pressure.

In a further study, the variable aperture restrictors, Flex I and Flex II were implanted in the porcine model as a part of a proof of concept study. The restrictors were implanted in growing pigs, which are constantly gaining weight. The goal of the study was therefore, to determine which type of aperture could safely reduce the amount of weight gain in the pigs.

Figure 11A:
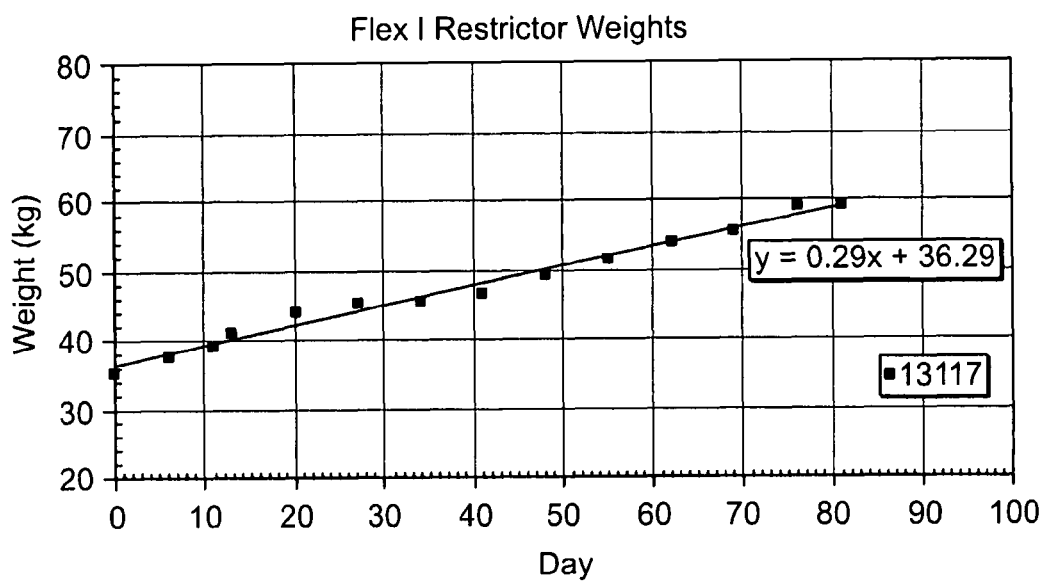
FIGS. 11A-11C illustrates the amount of weight loss as a result of different types of restrictors as tested on animals.
Figure 11B:
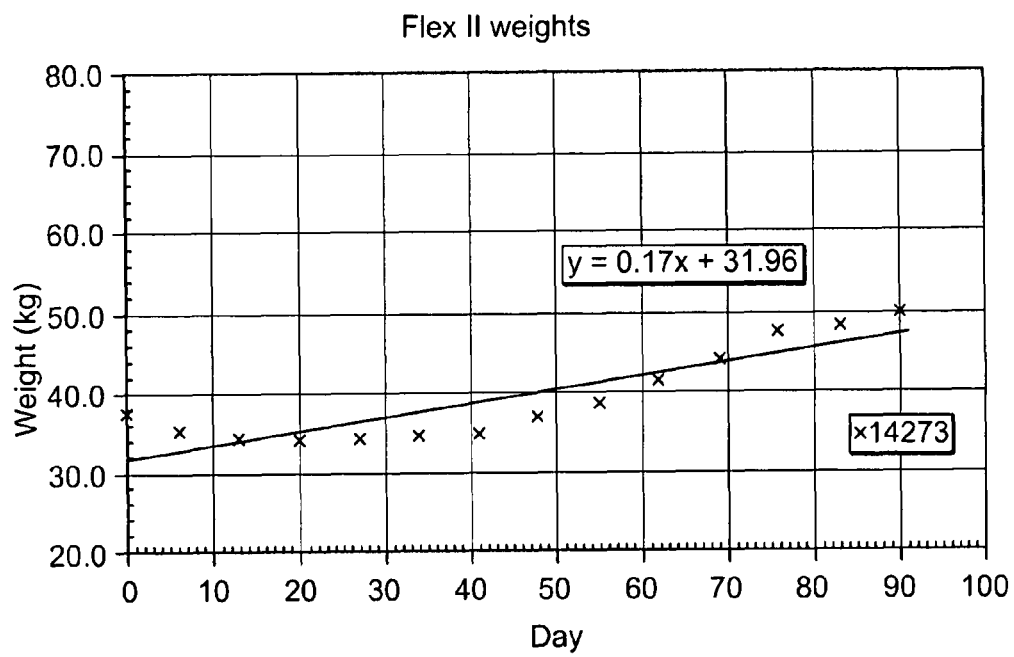

The results of the animal study are shown in FIGS. 11A and 11B. The charts illustrate the results of weight gain versus the number of days the Flex I and Flex II restrictors were implanted in the animal subjects. The charts further show equations for each variable aperture restrictor relating to the linear regressions of the respective data. The lower the slope of the line, the less is the weight gain per day and thus, the more effective is the device.

As shown in FIG. 11A, the average amount of weight gain for the pigs with the Flex I variable aperture was approximately 0.29 kg/day. The animals all ate normally within the implant period.

The Flex II model resulted in full gastric outlet obstruction by the sixth day due to its higher stiffness, but was successful in very few porcine models, one for which the results are shown in FIG. 11B. The average weight gain for the successful model was at approximately 0.17 kg/day. This device however, created an obstruction that the animal could not naturally resolve with increased pressure from the stomach. Additionally, in the Flex II study, the animal had eaten little to nothing over the implant period, yet the weight gain was not significantly reduced compared to Flex I, wherein the animals had eaten normally.

Figure 11C:
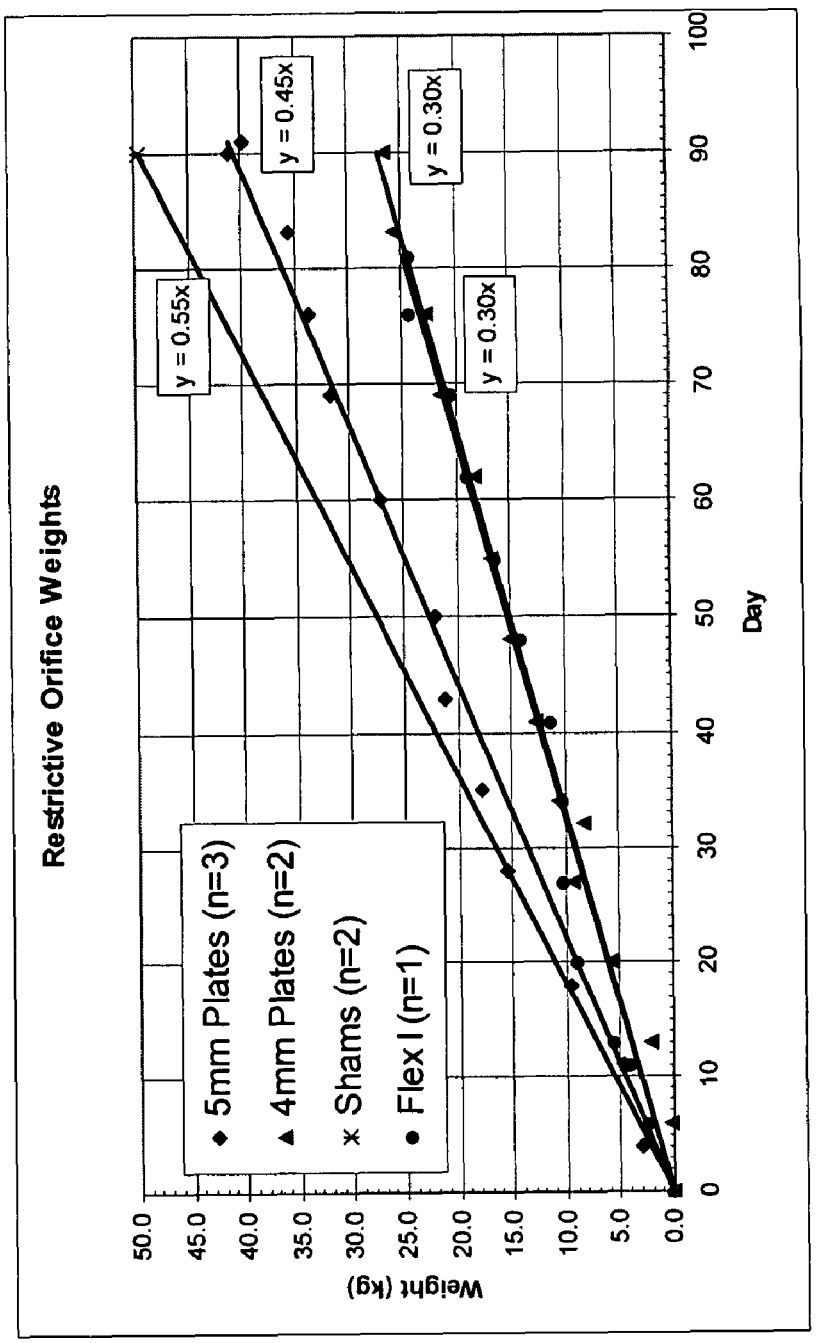

In FIG. 11C, a chart is shown comparing the results of static 5 mm and 4 mm restrictors, a sham (pig without any restrictive device implanted), and the Flex I variable aperture. The Flex I Restrictor significantly slowed weight gain without creating an obstruction or any other safety concern in comparison to the other apertures.

Based on these results, the preferred and safer embodiment for the variable aperture is one similar to the Flex I, with a lower durometer silicone. Thus, the preferred variable aperture has a steady-state inner diameter of less than 4 mm to create an adequate restriction, and an expandable inner diameter of greater than 7 mm to clear potential blockages. The silicone durometer is less than 30 A to achieve a desired expansion. The material need not be silicone, but can be any elastomeric material that is flexible and biocompatible such that it is stable for a long term implantation in the gastrointestinal tract. Alternatively or in addition, the variable aperture may be made of a circumferentially coiled spring.

Further, the variable aperture may be of a material and design such that additional material (like silicone) can be injected into or removed from the aperture to alter the steady-state inner diameter as desired. Additionally, the design may be such that concentric rings of varying diameter can be added or removed from the aperture to alter the diameter.

Figure 3:
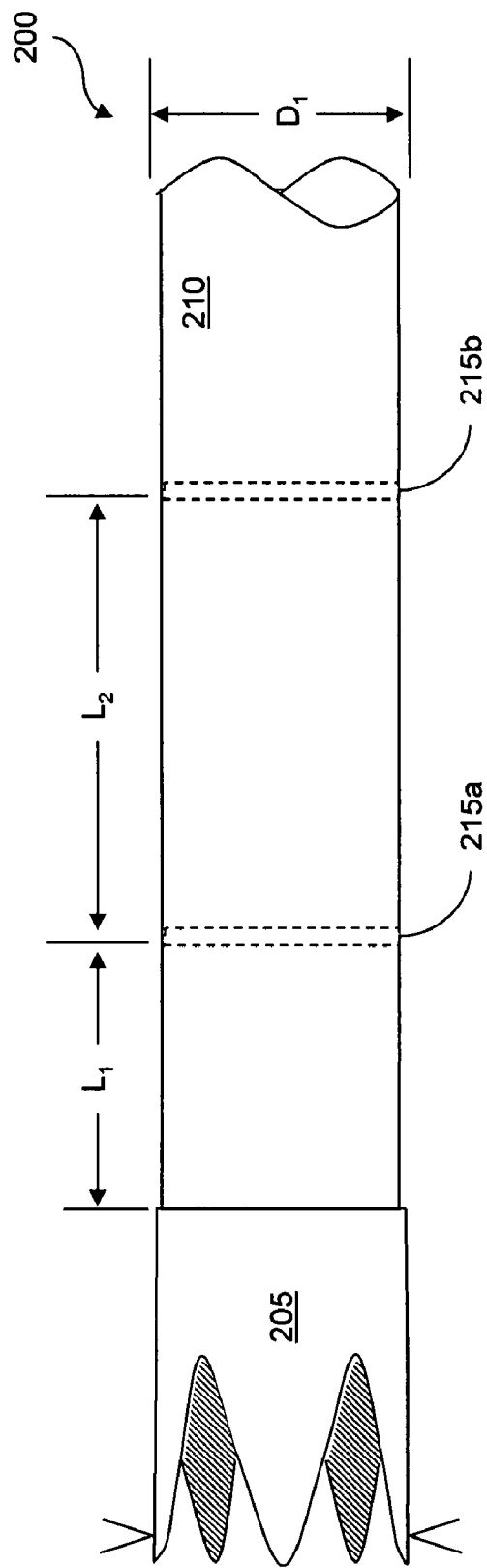
FIG. 3 is a side view of an embodiment of the invention including a sleeve having one or more restrictive members.

In some embodiments, the implant includes a sleeve. As shown in FIG. 3, an implant device 200 includes a flexible, floppy elongated sleeve 210 adapted for placement within a hollow organ, such as the intestine. In some embodiments, the implant 200 includes an anchor 205 coupled to the sleeve 210, with the anchor 205 adapted to secure at least a portion of the sleeve 210 within the lumen of the intestine. For example, a hollow anchor similar to those anchors described above can be attached to the proximal end of the sleeve 210 to secure the proximal end of the sleeve 210 to the surrounding tissue of the intestine. Once implanted, the sleeve 210 is extended distally from the anchor along the intestine.

Preferably, any of the implantable devices described herein can be configured to be removable. Thus, any permanence of a resistive device only applies during the period in which the device is implanted within the patient. Thus, a resistive device can be removed should the need arise. Alternatively or in addition, a different or even the same resistive device can be re-implanted within the same patient.

The sleeve 210 can be formed from a thin and conformable, yet durable biocompatible material and is generally unsupported and tending to collapse in the intestine to a small volume when empty. For example, the sleeve 210 can be formed from a fluoropolymer, such as expanded polytetrafluoroethylene (ePTFE). In some embodiments, the sleeve material is formed using a combination of different materials, such as ePTFE with a different fluoropolymer such as fluorinated ethylene propylene (FEP). The combination of ePTFE and FEP provides a low coefficient of friction, while also being substantially non-permeable. Alternatively or in addition, the sleeve is formed using polyolefin (e.g., LPDE, HPDE, polypropylene) films. Gastrointestinal sleeves are described in more detail in U.S. patent application Ser. No. 10/339,486, filed on Jan. 9, 2003, incorporated herein by reference in its entirety.

The sleeve 210 can have a diameter corresponding to the nominal expanded diameter of the lumen within which it is implanted. Current sleeves being used in porcine testing include diameters of about 25 millimeters, believed to be close to the diameter of the bowel. A sleeve having a similar diameter is also believed to be suitable for use within the proximal portion of the small intestine of an adult human. The length of the sleeve can vary from centimeters to a meter or more depending upon the particular application. Preferably the length of the sleeve is between one and five feet. The length should be such that the sleeve 210 extends over the ligament of Treitz beyond the proximal jejunum.

The sleeve 210 provides the added feature of preventing contact between the intestinal walls and any chyme contained therein. The sleeve can also delay the mixing of chyme with digestive enzymes secreted within the intestine.

The sleeve 210 can include one or more restrictive elements 215a, 215b (generally 215) positioned therein to partially block the intestinal lumen thereby impeding the flow of chyme and subsequently delaying emptying of the stomach. The restrictive elements 215 can include diaphragms that provide a partial blockage within the sleeve. For example, the diaphragm can be formed from an impermeable membrane defining an aperture or aperture that is smaller than the diameter of the sleeve 210. The diaphragms can have different orientations and configurations adapted to produce a desirable resistance to the flow of chyme within the sleeve 210.

The anchored sleeve 210 provides a framework for positioning and securing the diaphragms 215. As illustrated, a first diaphragm 215a is attached to the sleeve at a first distance $L_1$ measured distally from the proximal end of the sleeve. A second diaphragm 215b can optionally be attached to the sleeve 210 at a second distance $L_2$ measured distally from the first diaphragm 215a. The distal end of the sleeve 210 can terminate at the location of the last diaphragm 215 or optionally may extend further as illustrated.

Exemplary diaphragms 215 are described below and can be attached to the sleeve using any suitable method of attachment. For example, the diaphragms 215 can be attached using chemical fastening means, such as adhesives or thermal bonding. Alternatively or in addition, the diaphragms 215 can be attached using mechanical fastening means, such as sutures, staples, and clips.

The combination of an aperture and a sleeve is advantageous in achieving a larger amount of weight loss as compared to either device alone. An implant 1200 with a sleeve 1210 and an internal plate restrictor 1230 with an internal aperture 1220 is shown in FIG. 12.

Figure 12:
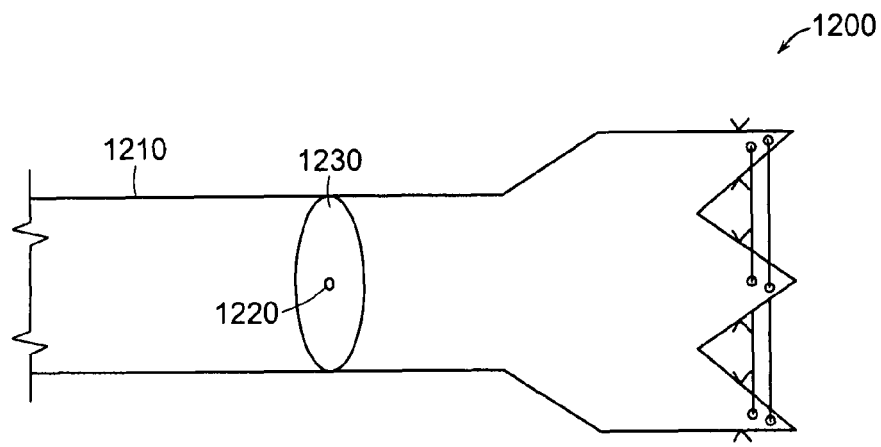
FIG. 12 shows an embodiment of a gastrointestinal device with a sleeve and restrictive aperture combination.
Figure 13:
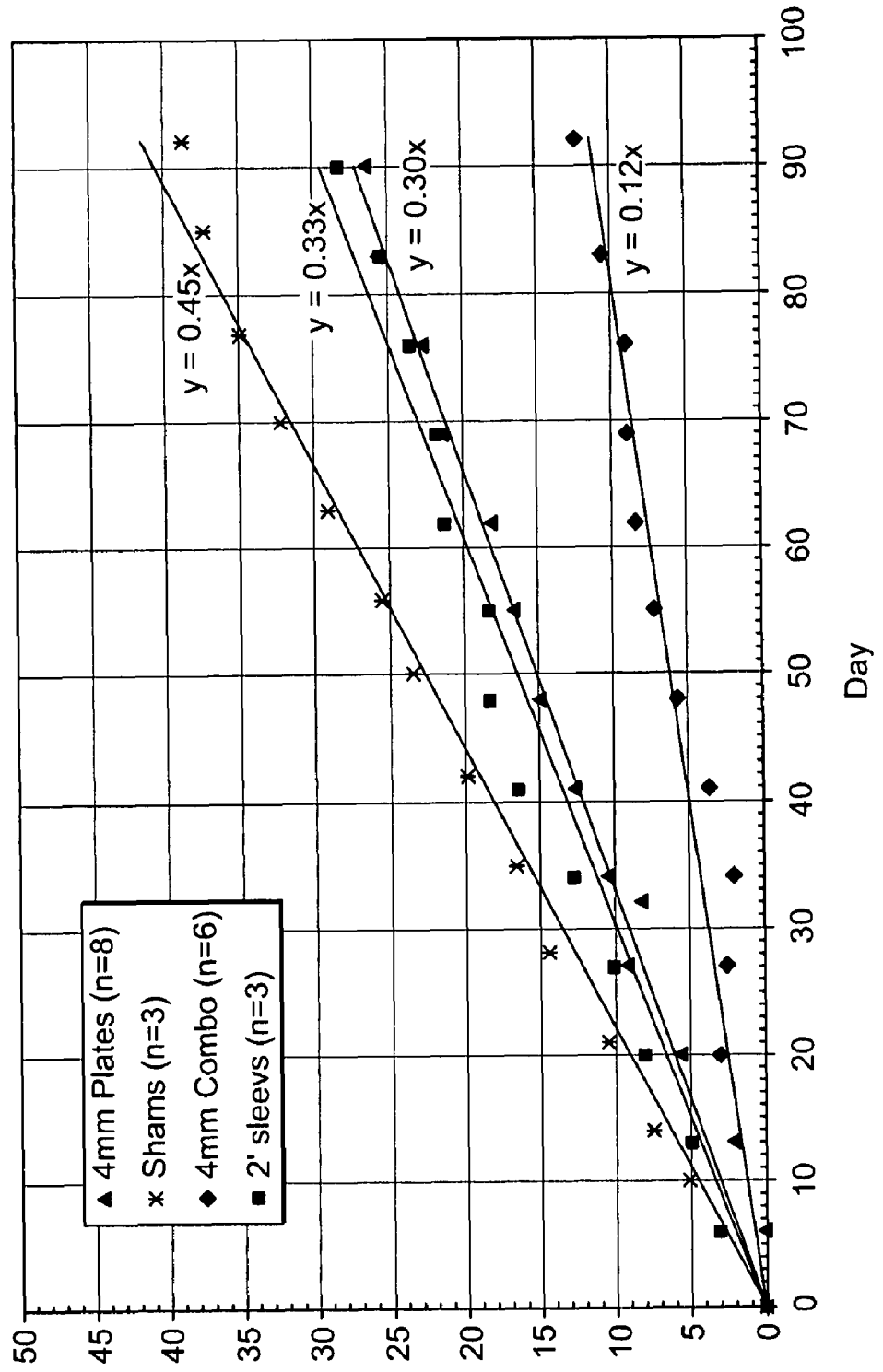
FIG. 13 illustrates the amount of weight loss as a result of different types of restrictors alone and in combination with an intestinal sleeve.

A study was conducted in porcine models comparing the reduction in the amount of weight gain with the implant 1200 including a 2 foot sleeve and a 4 mm plate aperture as shown in FIG. 12, a plate with a 4 mm aperture and no sleeve, a 2 foot sleeve on its own with no aperture, and a sham (an animal with no implant.) The results of the of the study are shown in FIG. 13.

As can be seen, the combination of the aperture 1220 and sleeve 1210 significantly reduced the amount of weight gain compared to either device alone. In fact, the weight loss (reduction of weight gain) for the combination was greater than the combined separate weight losses from the two individual devices, as apparent by the synergistic results. As stated previously, a lower slope indicates less weight gain and thus a more effective device. As can be seen, the slope of the combination device is approximate 0.12 as indicated by its equation (y=0.12x). The slopes of the individual devices are each more than double this (0.30 and 0.33) indicating that the combination device is more than twice as effective as either device used individually.

The aperture 1220 restricts the outflow of chyme from the stomach thus raising the pressure in the stomach. The chyme is then directed through the sleeve 1210, thus interrupting the digestion and the absorption process in the duodenum. By interrupting mixing of the chyme with juices in the duodenum, partially digested food material is not broken down into particles small enough to be absorbed by the body. Further, there is no mixing of bile with the chyme until the chyme reaches the jejunum. The absorption of fats and carbohydrates is reduced by delaying the mixing of bile with the chyme.

Thus, with the combination device 1200, two mechanisms are acting to reduce obesity; the aperture 1220 to raise stomach pressure by restricting chyme from the stomach, and the sleeve 1210 to bypass a portion of the intestine to reduce the absorption of nutrients.

The diaphragm with the aperture can take on any conceivable shape. Exemplary diaphragms are shown in FIGS. 4A through 4D. A diaphragm 300 defining a single aperture or aperture 305 is shown in FIG. 4A. The aperture 305 is defined within a diaphragm providing a closed surface 300. The aperture 305 provides a reduced-diameter stricture. The aperture 305 can further be an elastomeric or variable aperture as shown in FIGS. 8A and 8B.

In another embodiment shown in FIG. 4C, the diaphragm 320 includes more than one smaller apertures 325. The number and size of the apertures 325 can be used to control the percent blockage of the lumen resulting in resistance to the flow of chyme. Additionally, the diameter of the apertures 325 themselves can be used to provide further resistance by limiting the size of solids allowed to pass. For example, multiple circular apertures 325 can be distributed in a regular or irregular pattern across the surface of the diaphragm 320.

In some embodiments, the diameter of the diaphragm is about 25 mm, corresponding to the internal diameter of the sleeve, with each aperture 325 having a respective smaller diameter (e.g., about 3 millimeters or less). Alternatively or in addition, the size of the aperture can be increased by removing one or more portions of the diaphragm between groups of apertures 325. Such alterations can be accomplished prior to implantation of the device, or in situ using an endoscope. The material can be removed or the aperture otherwise enlarged by selectively cutting the material between different apertures. In some embodiments, perforations 326 are provided between different apertures 325 and along the diaphragm itself to facilitate alterations.

In yet other embodiments, the diaphragm 330 includes a screen or sieve as illustrated in FIG. 4D. A screen or sieve 335 can be coupled to a frame 330 to facilitation attachment to the diaphragm 330 to the sleeve.

Figure 5:
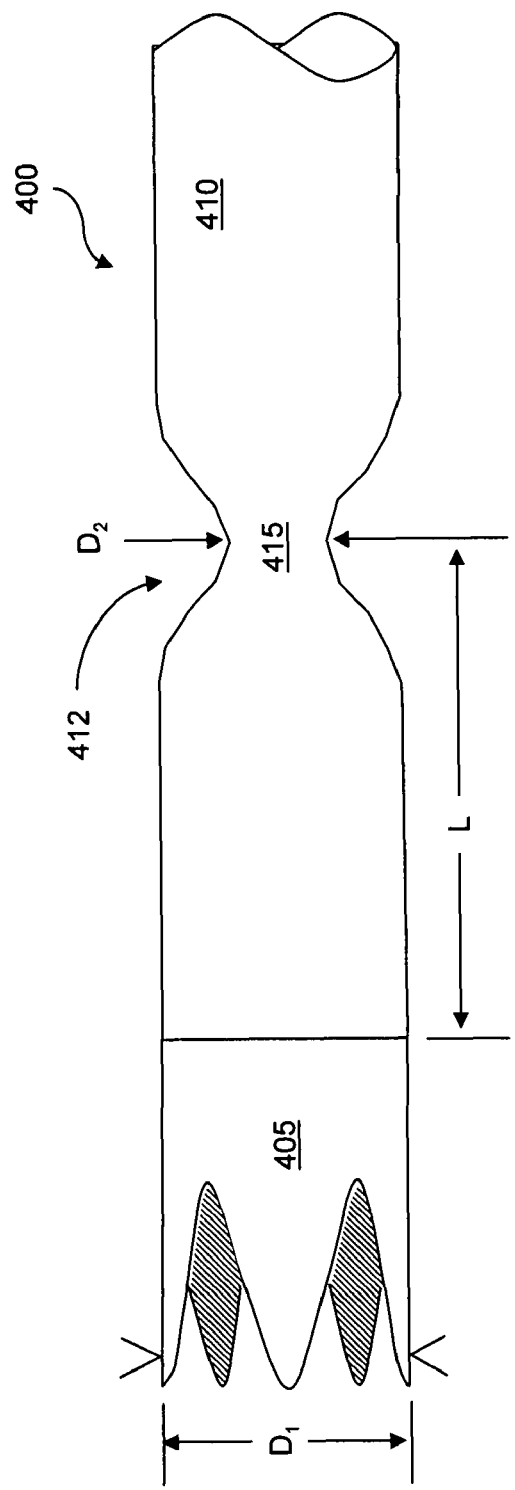
FIG. 5 is a schematic diagram illustrating an embodiment of the invention including a sleeve having a narrowed region.

Alternatively or in addition, an artificial stricture can be created within the sleeve itself. An exemplary sleeve-based stricture device 400 is shown in FIG. 5. The device 400 includes an elongated sleeve 410 having an internal diameter and defining a reduced diameter over at least a portion of the sleeve length. In some embodiments, the device 400 includes an anchor 405 coupled to the proximal end of the elongated sleeve 410 to retain the device within the gastrointestinal tract when implanted therein as described above. The sleeve 410 contains an axial region 412 having a reduced diameter to provide a permanent restrictor 415. For instance, the sleeve 410 could be reduced in diameter forming the hourglass configuration shown. Thus, the elongated sleeve's diameter measured along its axis transitions from a first diameter $D_1$ (e.g., 25 millimeters), at a proximal end and for a predetermined length L along the sleeve, to a lesser diameter $D_2$ (e.g., about 3 to 10 millimeters). The reduced diameter persists at least briefly, and then may or may not transition back again to a larger diameter (e.g., back to $D_1$).

In some embodiments the lesser diameter (e.g., $D_2$) persists for only a short distance resulting in the hourglass configuration; whereas, in other embodiments the reduced diameter may extend for a predetermined length along the axis. The resulting reduced diameter provides a permanent stricture, or narrowed aperture, tending to slow gastric emptying by reducing the rate at which chyme flows through the aperture and consequently through any portion of the intestine proximal to the aperture.

In another embodiment, not shown, substantially the entire length of the sleeve can be sized having a diameter smaller than would otherwise be provided by the intestine alone. For example, a sleeve defining a central lumen with a diameter less than 25 millimeters (e.g., between about 5 and 20 millimeters) would also impede the flow of chyme by increasing its flow resistance.

Alternatively or in addition, the length of the sleeve can slow gastric emptying. Some test observations indicate that animals having longer sleeve implants (e.g., 4 ft, or about 1.2 meters) appear to eat less, or at least less quickly, than do animals with similar, but shorter sleeves (e.g., 2 ft, or about 0.6 meters). At least one reason that the length of the sleeve matters is that the longer the sleeve, the slower the propagation of chyme through it. An animal may have a greater sense of fullness as the chyme winds through the intestines more slowly. Also, the intestines may need to work harder to pass the chyme. Thus, the sleeve length can affect energy expenditure directly.

In addition to simply providing a narrower channel through which chyme will flow, the sleeve can reduce the efficiency of natural peristalsis. Peristalsis refers to the forces exerted by the intestine to mix and pass chyme distally through the intestine. In the presence of a sleeve, peristaltic forces provided by the intestine must operate upon the chyme through the sleeve material. Preferably, the sleeve is adapted to channel most if not all of the chyme through its central lumen.

In some embodiments, it may be desirable to have a relatively flexible sleeve near the bile and pancreatic ducts so as not to block the ampulla of vater, but a stiffer material more distal, to increase resistance to flow. Thus, the properties of the sleeve material can be varied along the sleeve. For example, the same material can be provided with various thicknesses to control variations in the damping performance of the sleeve along its axis. Alternatively or in addition, different materials can be combined to provide the desired values. Configurations can include overlapping portions of the same and/or different materials and/or adjacent regions formed from different materials.

Figure 6:
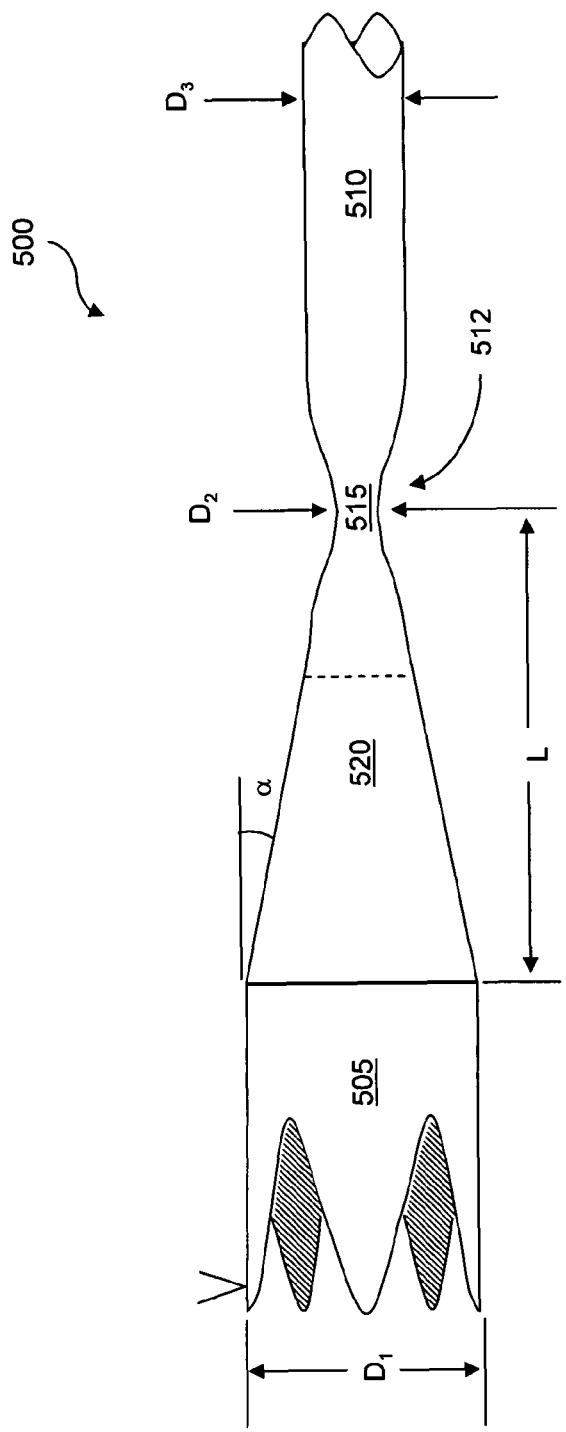
FIG. 6 is a schematic diagram illustrating an alternative embodiment of the invention including a tapered segment and a narrowed region.

In an alternative embodiment shown in FIG. 6, an implantable device 500 includes a restrictor formed by a sleeve 510 coupled at its proximal end to an anchor 505 adapted to anchor the sleeve with the gastrointestinal tract. In particular, the device 500 includes an aperture 515 having a reduced diameter $D_2$, similar to that describe above in relation to FIG. 5. Additionally, however, the device 500 includes a tapered sleeve segment 520 between the anchor and the aperture 515. The tapered segment 520 transitions a first diameter $D_1$ to a lesser diameter by "necking down" a proximal portion of the device. The tapered segment 520 can be accomplished in a reinforced region of the sleeve just distal to the anchor 505. Such a restrictor provides a permanent orifice, of a diameter less than the natural lumen, thereby slowing gastric emptying. It is believed that the tapered region 520 will reduce the loss of water from the chyme suspension that might otherwise occur in a more abrupt transition.

Alternatively or in addition to aperture type restrictors, other types of variable restrictors may be used in a gastrointestinal implant. These devices are designed to open to a large aperture diameter in response to elevated pressures so as to release the cause of the pressure, presumably an obstruction in the device. If the device obstructs, the stomach pressure will rise. The aperture of the device then snaps open to relieve the pressure. Once the pressure drops, the aperture then closes back to the desired and original aperture size.

Figure 14A:
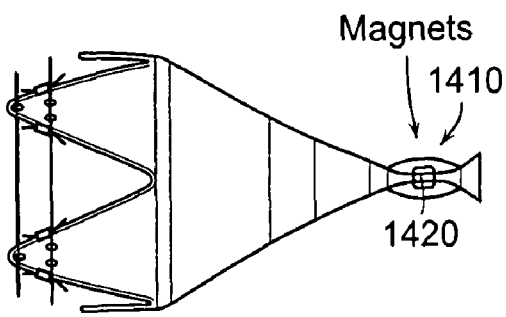
FIGS. 14A and 14B illustrate an alternative embodiment of an implantable device using magnets.
Figure 14B:
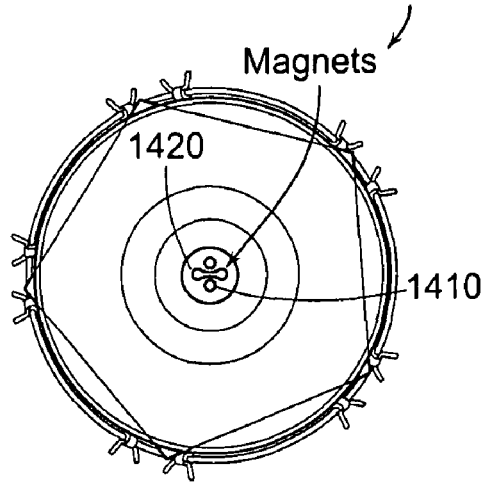

As shown in FIGS. 14A and 14B, one embodiment of a gastrointestinal implant 1400 includes the use of magnets 1410 to hold sleeve material collapsed around the aperture 1420. The magnets 1410 separate under elevated physiological pressure. For example, if the expanded diameter of the aperture 1420 at the location of the magnets is 10 mm, and the magnets 1410 have a diameter of about 5 mm, then when collapsed, the effective open diameter of the aperture is about 5 mm as the magnets 1410 take up the space of their diameter. When the pressure rises and the magnets 1410 separate, the aperture 1420 opens up to its maximum diameter. Once the pressure is relieved, the magnets 1410 come back together to reduce the diameter of the aperture 1420.

Figure 15:
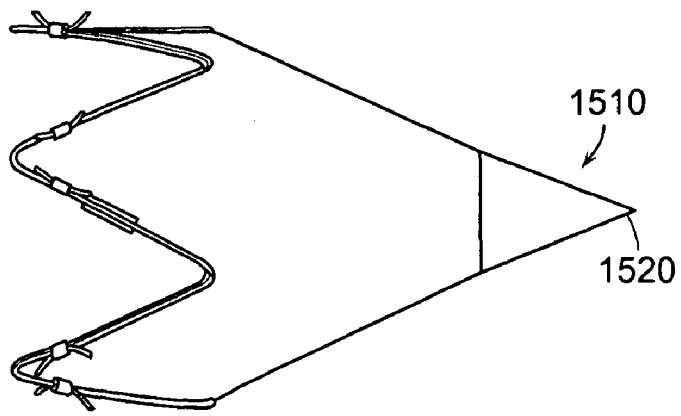
FIG. 15 illustrates an alternative embodiment of an implantable device with a duck-bill valve.

FIG. 15 shows an alternative embodiment of a gastrointestinal implant 1500 using a duckbill valve 1510 of elastomeric material. This valve 1510 is normally closed with a small distal opening 1520 of the desired orifice size (for example of about 4 mm). As the pressure rises, two leaves of the valve 1510 open, thus relieving the pressure. Once the pressure is relieved, the valve 1510 returns to its normal closed size.

Figure 16A:
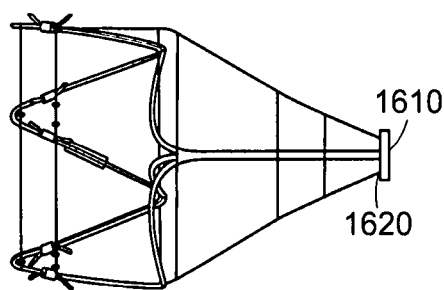
FIGS. 16A and 16B illustrate an alternative embodiment of an implantable device with a piston.
Figure 16B:
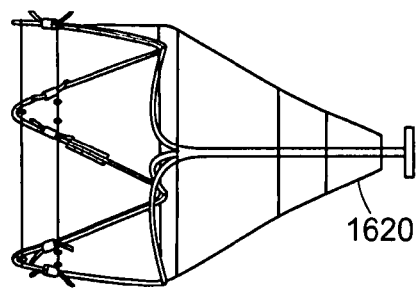

FIGS. 16A and 16B show an alternative embodiment of the device using a piston 1610 that seals the aperture 1620 closed. The piston 1610 may work in two ways. It may completely occlude the aperture 1620 so that no flow occurs until stomach pressures rise above normal pressures as is shown in FIG. 16A. The piston 1610 then opens the aperture 1620 under increased pressure as is shown in FIG. 16B.

In an alternative embodiment (not shown), the piston 1610 may have a small hole in it (for example of about 4 mm), to permit flow when closed. In this way, the piston 1610 will open when pressure rises when the orifice occludes. The piston 1610 will then open fully and release the obstruction from the aperture 1620.

Figure 19:
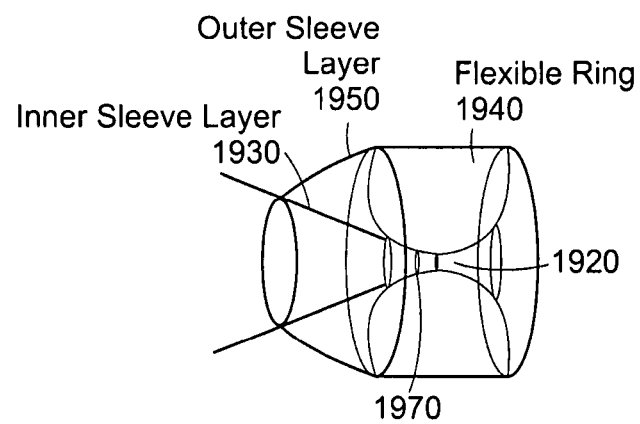
FIG. 19 illustrates the assembly of an embodiment of an implantable device with a variable aperture.

FIG. 19 illustrates how the variable aperture of FIGS. 8A-8B is assembled. A variable aperture 1920 component is assembled such that it is entirely sealed within sleeve material. In this way, the material of the variable aperture has no direct contact with the fluids in the gastrointestinal tract and is therefore less likely to deteriorate over time.

The assembly of the variable aperture is as follows. A sleeve material (such as EPTFE) or an inner sleeve layer 1930 is wound on a 10 mm mandrel to create a tube 1970. A flexible ring 1940 is then stretched over the mandrel and placed at midpoint of tube. Another layer of sleeve material or an outer sleeve material is then wound over the flexible ring 1940 to create an outer sleeve layer 1950. The goal is to create a variable aperture 1920 that at rest is restricted by the flexible ring 1940 to a diameter between 1 mm-4 mm, but will allow the ring to expand to a maximum diameter of 10 mm without constraint under elevated physiological pressures.

While this invention has been particularly shown and described with references to preferred embodiments thereof, it will be understood by those skilled in the art that various changes in form and details may be made therein without departing from the scope of the invention encompassed by the appended claims. It should also be appreciated that the various features of the embodiments that have been described may be combined in various ways to produce numerous additional embodiments. Moreover, while various materials, dimensions, shapes, implantation locations, types of anchors, etc. have been described for use with the disclosed embodiments, others besides those disclosed may be utilized without extending the scope of the invention, including implantation locations in or above the pylorus.

What is claimed is:

1. A gastrointestinal implant device comprising:
    an anchor adapted to be retained in the pyloric orifice or distal to the pylorus; and
    a restrictive aperture attached to the anchor, adapted to retard the outflow of chyme from the stomach, the aperture expanding substantially at a pressure of 50 inches of water or more, the diameter of the aperture being about 5 mm or below, when the water pressure is between 0 and 50 inches of water.

2. The gastrointestinal implant device of claim 1, wherein the aperture ranges in diameter from 1 to 10 millimeters over a range of water pressures.

3. The gastrointestinal implant device of claim 1, wherein the diameter of the aperture is about 4 mm or below, when the water pressure is between 0 inches and 50 inches of water.

4. The gastrointestinal implant device of claim 1, wherein the diameter of the aperture opens to greater than 4 mm when the water pressure is above 50 inches of water.

5. The gastrointestinal implant device of claim 1, wherein the aperture is made of silicone.

6. The gastrointestinal implant device of claim 1, further comprising a flexible and floppy sleeve that is in communication with the anchor.

7. The gastrointestinal implant device of claim 6, wherein the aperture is within the sleeve.

8. The gastrointestinal implant device of claim 6, wherein the sleeve is at least one foot in length to extend into the intestine.

9. A gastrointestinal implant device comprising:
   an anchor adapted to be retained in the pyloric orifice or distal to the pylorus;
   a flexible, floppy sleeve, a proximal end of the sleeve attached to the anchor, the sleeve to extend into the intestine, the sleeve defining a lumen through which chyme passes; and
   a restricting aperture within the sleeve, the aperture adapted to retard the outflow of chyme from the stomach, the aperture expanding substantially at a pressure of 50 inches of water or more, the diameter of the aperture being about 5 mm or below, when the water pressure is between 0 and 50 inches of water.

10. The gastrointestinal implant device of claim 9, wherein the aperture ranges in diameter from 1 to 10 millimeters over a range of water pressure.

11. The gastrointestinal implant device of claim 9, wherein the diameter of the aperture is about 4 mm or below, when the water pressure is between 0 inches and 50 inches of water.

12. The gastrointestinal implant device of claim 9, wherein the diameter of the aperture opens to greater than 4 mm when the water pressure is above 50 inches of water.

13. The gastrointestinal implant device of claim 9, wherein the aperture is made of silicone.

14. The gastrointestinal implant device of claim 9, wherein the sleeve encapsulates the anchor and the aperture.

15. The gastrointestinal implant device of claim 9, wherein the sleeve is at least one foot in length to extend into the intestine.

16. A method for treating obesity comprising:
   implanting a device within a gastrointestinal tract of an animal at or distal to the pylorus; and
   with the implanted device, resisting the outflow of chyme from the stomach with a restrictive aperture, the aperture expanding substantially at a pressure of 50 inches of water or more, the diameter of the aperture being about 5 mm or below, when the water pressure is between 0 and 50 inches of water.

17. The method of claim 16, wherein the aperture ranges in diameter from 1 to 10 millimeters over a range of water pressures.

18. The method of claim 16, wherein the diameter of the aperture is about 4 mm or below, when the water pressure is between 0 inches and 50 inches of water.

19. The method of claim 16, wherein the diameter of the aperture opens to greater than 4 mm when the water pressure is above 50 inches of water.

20. The method of claim 16, wherein the aperture is made of silicone.

21. The method of claim 16, further comprising a flexible and floppy sleeve that is in communication with the anchor.

22. The method of claim 21, wherein the aperture is within the sleeve.

23. The method of claim 22, wherein the sleeve is at least one foot in length to extend into the intestine.

24. A method of treating obesity comprising:
   anchoring a flexible, floppy sleeve with an anchor in the intestine, the sleeve extending into the intestine, the sleeve defining a lumen through which chyme passes; and
   restricting the outflow of chyme from the stomach with a restrictive aperture within the sleeve, the aperture expanding substantially at a pressure of 50 inches of water or more, the diameter of the aperture being about 5 mm or below, when the water pressure is between 0 and 50 inches of water.

25. The method of claim 24, wherein the aperture ranges in diameter from 1 to 10 millimeters over a range of water pressure.

26. The method of claim 24, wherein the diameter of the aperture is about 4 mm or below, when the water pressure is between 0 inches and 50 inches of water.

27. The method of claim 24, wherein the diameter of the aperture opens to greater than 4 mm when the water pressure is above 50 inches of water.

28. The method of claim 24, wherein the aperture is made of silicone.

29. The method of claim 24, wherein the sleeve encapsulates the anchor and the aperture.

30. The method of claim 24, wherein the sleeve is at least one foot in length to extend into the intestine.

31. The method of claim 24, wherein the anchor is retained within the pyloric orifice.

32. The method of claim 24, wherein the anchor is retained distal to the pylorus.

33. The method of claim 24, wherein the implanting step comprises removably anchoring the device within the gastrointestinal tract.

34. A gastrointestinal implant for treating obesity comprising:
   aperture means for increasing within the intestine resistance to the outflow of chyme from the stomach, the aperture expanding substantially at a pressure of 50 inches of water or more, the diameter of the aperture being about 5 mm or below, when the water pressure is between 0 and 50 inches of water; and
   anchoring means for anchoring within a gastrointestinal tract of an animal and at the pyloric orifice or distal to the pylorus the aperture means.

35. The gastrointestinal implant of claim 34 further comprising flexible, floppy sleeve means attached to the anchor, the sleeve means to extend into the intestine, and the sleeve means defining a lumen through which chyme passes.

* * * * *